(12) United States Patent
Qin et al.

(10) Patent No.: US 12,042,561 B2
(45) Date of Patent: Jul. 23, 2024

(54) HYDROPHOBIC MOLECULE-INDUCED BRANCHED POLYMER AGGREGATES AND THEIR USE

(71) Applicant: ANP Technologies, Inc., Newark, DE (US)

(72) Inventors: Dujie Qin, Wilmington, DE (US); Ray Yin, Wilmington, DE (US); Jing Pan, Newark, DE (US); Yubei Zhang, Hockessin, DE (US)

(73) Assignee: ANP Technologies, Inc., Newark, DE (US)

( * ) Notice: Subject to any disclaimer, the term of this patent is extended or adjusted under 35 U.S.C. 154(b) by 0 days.

(21) Appl. No.: 16/900,978

(22) Filed: Jun. 14, 2020

(65) Prior Publication Data

US 2021/0059939 A1    Mar. 4, 2021

Related U.S. Application Data

(62) Division of application No. 15/818,742, filed on Nov. 21, 2017, now Pat. No. 10,688,048, which is a division of application No. 13/978,713, filed as application No. PCT/US2012/020524 on Jan. 6, 2012, now abandoned.

(60) Provisional application No. 61/502,793, filed on Jun. 29, 2011, provisional application No. 61/500,633, filed on Jun. 24, 2011, provisional application No. 61/431,042, filed on Jan. 9, 2011.

(51) Int. Cl.

| | |
|---|---|
| *A61K 9/14* | (2006.01) |
| *A61K 9/19* | (2006.01) |
| *A61K 9/51* | (2006.01) |
| *A61K 31/337* | (2006.01) |
| *A61K 31/4375* | (2006.01) |
| *A61K 31/4745* | (2006.01) |
| *A61K 33/243* | (2019.01) |
| *A61K 45/06* | (2006.01) |
| *A61K 47/34* | (2017.01) |
| *A61K 47/58* | (2017.01) |
| *A61K 47/59* | (2017.01) |
| *A61K 47/68* | (2017.01) |
| *A61K 49/00* | (2006.01) |
| *A61K 49/12* | (2006.01) |
| *A61K 51/06* | (2006.01) |

(52) U.S. Cl.
CPC ............... *A61K 9/14* (2013.01); *A61K 9/19* (2013.01); *A61K 9/513* (2013.01); *A61K 9/5146* (2013.01); *A61K 31/337* (2013.01); *A61K 31/4375* (2013.01); *A61K 31/4745* (2013.01); *A61K 33/243* (2019.01); *A61K 45/06* (2013.01); *A61K 47/34* (2013.01); *A61K 47/58* (2017.08); *A61K 47/59* (2017.08); *A61K 47/6803* (2017.08); *A61K 49/0004* (2013.01); *A61K 49/12* (2013.01); *A61K 51/06* (2013.01)

(58) Field of Classification Search
CPC .......... A61K 9/14; A61K 49/12; A61K 47/59
See application file for complete search history.

(56) References Cited

U.S. PATENT DOCUMENTS

| | | |
|---|---|---|
| 5,919,442 A | 7/1999 | Yin et al. |
| 6,177,414 B1 | 1/2001 | Tomalia et al. |
| 7,169,793 B2 | 1/2007 | Reddy et al. |
| 7,754,500 B2 | 7/2010 | Yin et al. |
| 2002/0041888 A1 | 4/2002 | Flashner-Barak et al. |
| 2002/0041898 A1 | 4/2002 | Unger et al. |
| 2004/0009229 A1 | 1/2004 | Unger et al. |
| 2006/0041058 A1 | 2/2006 | Yin et al. |
| 2006/0051315 A1 | 3/2006 | Scaria et al. |
| 2006/0127350 A1 | 6/2006 | Heegaard et al. |
| 2006/0188579 A1 | 8/2006 | Rogueda |
| 2008/0114077 A1 | 5/2008 | Yin et al. |
| 2008/0200562 A1 | 8/2008 | Yin et al. |
| 2011/0060036 A1 | 3/2011 | Nie et al. |
| 2014/0314664 A1 | 10/2014 | Qin et al. |

OTHER PUBLICATIONS http://www.merriamwebster.com/dictionary/derivative (Year: 2015).*
Tan et al., "Aggregation . . . dendrimer," Eur Phy J E 27:205-211, 2008.
Hoogenboom et al., "Poly . . . applications," Ang Chem Inter Ed 48:7978-7994, 2009.
D'Emanuele et al., "Dendrimer-drug Interaction," Adv Drug Del News 57:2147-2162, 2005.
Wolinsky et al., "Therapeutic . . . treatment," Adv Drug Del Rev 60:1037-1055, 2008.
Cheng et al., "New insight . . . aggregation," J Phys Chem B 113:8339-8346, 2009.
Gillies et al., "pH-Responsive . . . doxorubicin," Bioconj Chem 16:361-368, 2005.

* cited by examiner

*Primary Examiner* — James W Rogers
(74) *Attorney, Agent, or Firm* — MDIP LLC; Gann G Xu

(57) ABSTRACT

Symmetrically and asymmetrically branched homopolymers are modified at the surface level with functional groups that enable forming aggregates with water insoluble or poorly water soluble pharmaceutically active agents (PAA). The aggregates formed are specifically induced by interaction of PAA and homopolymer and are different from aggregates that are formed by the polymer alone in the absence of the PAA or by the PAA alone in the absence of the polymer. Such aggregates can be used to improve drug solubility, stability, delivery and efficacy.

8 Claims, 19 Drawing Sheets

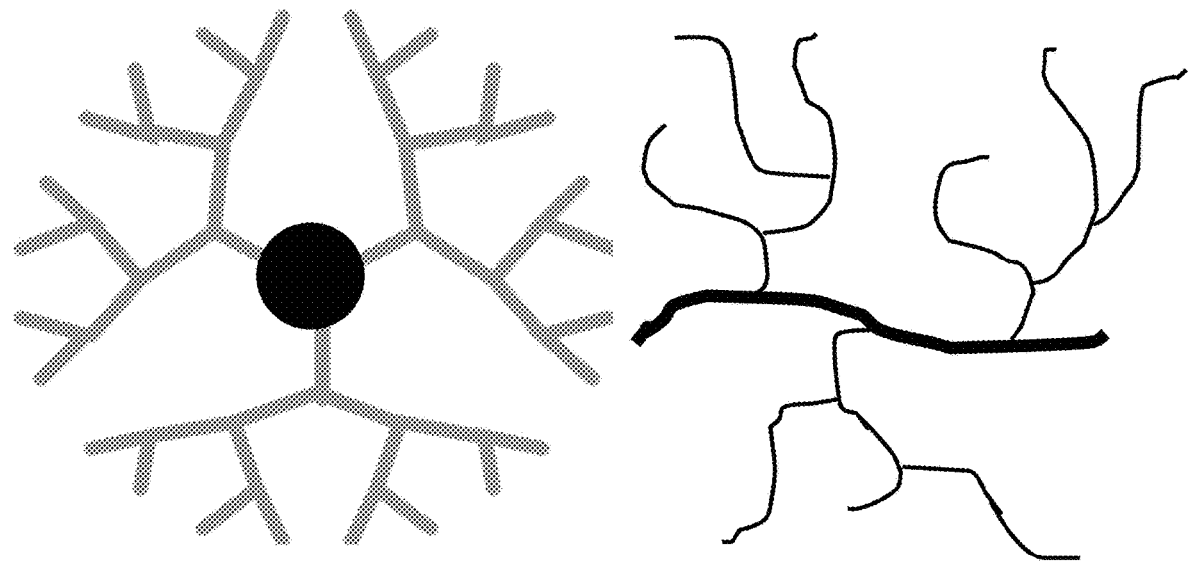
Dendrimers
Fig. 1A
Dendrigrafts
Fig. 1B
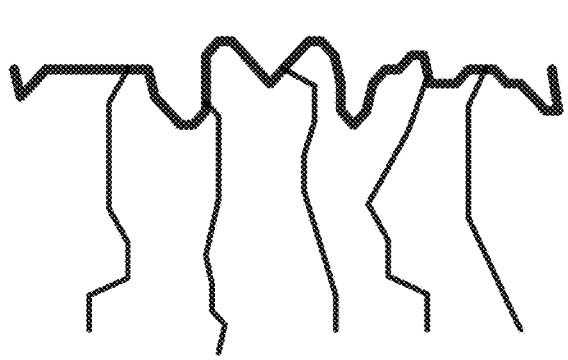
Regular Comb-branches
Fig. 1C
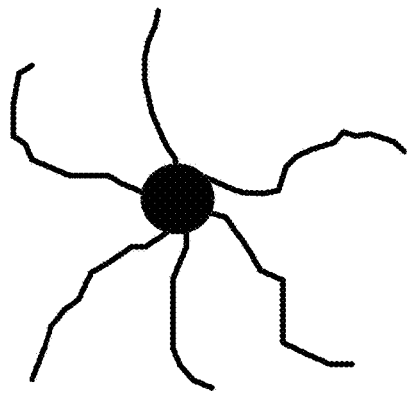
Star-branched
Fig. 1D

Polypropyleneimine Dendrimer-4

Polypropyleneimine Dendrimer-8

Random ABP    Regular ABP

HYDROPHOBIC MOLECULE-INDUCED BRANCHED POLYMER AGGREGATES AND THEIR USE

The instant application claims benefit to U.S. Ser. No. 61/431,042 filed 9 Jan. 2011, U.S. Ser. No. 61/500,633 filed 24 Jun. 2011, and U.S. Ser. No. 61/502,793 filed 29 Jun. 2011, the content of each of which is incorporated herein by reference in entirety.

FIELD

The present disclosure relates to a surface modified branched polymer (MBP), which can either be a surface modified symmetrically branched polymer (SBP) or a surface modified asymmetrically branched polymer (ABP), which on exposure to a water insoluble or poorly water soluble molecule, such as, a drug, forms a composite nanoparticle or nanoaggregate, wherein the drug is dispersed or deposited primarily at the surface of the structures where hydrophobic portions or sites are located. The particles or aggregates of interest are stable, for example, can be desiccated and rehydrated. The nanoparticles or nanoaggregates can range from about 50 nm to about 500 nm in diameter depending, in part, on the drug to polymer ratio, the drug, the polymer, the solvent(s) used, amount of the homopolymer and amount of the drug. Hydrophobic, electrostatic, metal-ligand interactions, hydrogen bonding and other molecular interactions may be involved in the spontaneous interactions between the water insoluble or poorly water soluble molecule and the homopolymer to form aggregates. The particles or aggregates of interest have a controlled release profile and thus find utility, for example, as a carrier for the controlled release of pharmacologically active agents, drugs and the like in a host, for providing a supplement, nutrient or requirement; for treating any of a variety of disorders; and the like.

BACKGROUND

Symmetrically Branched Polymers

A new class of polymers called dendritic polymers, including Starburst dendrimers (or Dense Star polymers) and Combburst dendrigrafts (or hyper comb branched polymers), recently was developed and studied for various industrial applications. Those polymers often possess: (a) a well defined core molecule, (b) at least two concentric dendritic layers (generations) with symmetrical (equal length) branches and branch junctures, and (c) exterior surface groups, such as, polyamidoamine (PAMAM)-based branched polymers and dendrimers described in U.S. Pat. Nos. 4,435,548; 4,507,466; 4,568,737; 4,587,329; 5,338,532; 5,527,524; and 5,714,166. Other examples include polyethyleneimine (PEI) dendrimers, such as those disclosed in U.S. Pat. No. 4,631,337; polypropyleneimine (PPI) dendrimers, such as those disclosed in U.S. Pat. Nos. 5,530,092; 5,610,268; and 5,698,662; Frechet-type polyether and polyester dendrimers, core shell tectodendrimers and others, as described, for example, in "Dendritic Molecules", edited by Newkome et al., VCH Weinheim, 1996; "Dendrimers and Other Dendritic Polymers", edited by Frechet & Tomalia, John Wiley & Sons, Ltd., 2001; and U.S. Pat. No. 7,754,500.

Combburst dendrigrafts are constructed with a core molecule and concentric layers with symmetrical branches through a stepwise synthetic method. In contrast to dendrimers, Combburst dendrigrafts or polymers are generated with monodisperse linear polymeric building blocks (U.S. Pat. Nos. 5,773,527; 5,631,329 and 5,919,442). Moreover, the branch pattern is different from that of dendrimers. For example, Combburst dendrigrafts form branch junctures along the polymeric backbones (chain branches), while Starburst dendrimers often branch at the termini (terminal branches). Due to the living polymerization techniques used, the molecular weight distributions ($M_w/M_n$) of those polymers (core and branches) often are narrow. Thus, Combburst dendrigrafts produced through a graft-on-graft process are well defined with $M_w/M_n$ ratios often less than about 1.

SBP's, such as dendrimers, are predominantly produced by repetitive protecting and deprotecting procedures through either a divergent or a convergent synthetic approach. Since dendrimers utilize small molecules as building blocks for the cores and the branches, the molecular weight distribution of the dendrimers often is defined. In the case of lower generations, a single molecular weight dendrimer often is obtained.

In addition to dendrimers and dendrigrafts, other SBP's include symmetrical star shaped or comb shaped polymers, such as, symmetrical star shaped or comb shaped polyethyleneoxide (PEO), polyethyleneglycol (PEG), PEI, PPI, polyoxazoline (PDX), polymethyloxazoline (PMOX), polyethyloxazoline (PEOX), polystyrene, polymethylmethacrylate, polydimethylsiloxane or a combination thereof.

Asymmetrically Branched Polymers

Unlike SBP's, asymmetrically branched polymers (ABP), particularly asymmetrically branched dendrimers or regular ABP (reg-ABP), often possess a core, controlled and well defined asymmetrical (unequal length) branches and asymmetrical branch junctures as described in U.S. Pat. Nos. 4,289,872; 4,360,646; and 4,410,688.

On the other hand, a random ABP (ran-ABP) possesses: a) no core, b) functional groups both at the exterior and in the interior, c) random/variable branch lengths and patterns (i.e., termini and chain branches), and d) unevenly distributed interior void spaces.

The synthesis and mechanisms of ran-ABPs, such as, made of PEI, was reported by Jones et al., J. Org. Chem. 9, 125 (1944), Jones et al., J. Org. Chem. 30, 1994 (1965) and Dick et al., J. Macromol. Sci. Chem., A4 (6), 1301-1314, (1970)). Ran-ABP, such as those made of PDX, i.e., poly (2-methyloxazoline) and poly(2-ethyloxazoline), were reported by Litt (J. Macromol. Sci. Chem. A9(5), 703-727 (1975)) and Warakomski (J. Polym. Sci. Polym. Chem. 28, 3551 (1990)). The synthesis of ran-ABP's often can involve a one-pot divergent or a one-pot convergent method.

Homopolymers

A homopolymer can relate to a polymer or to a polymer backbone composed of the same repeat unit, that is, the hompolymer is generated from the same monomer (e.g., polyethyleneimine dendrimers, polyamidoamine dendrimers or polyoxazoline dendrimers). The monomer can be a simple compound or a complex or an assemblage of compounds where the assemblage or complex is the repeat unit in the homopolymer. Thus, if an assemblage is composed of three compounds, A, B and C; the complex can be depicted as ABC. A polymer composed of (ABC)-(ABC)-(ABC) . . . is a homopolymer for the purposes of the instant disclosure. The homopolymer may be linear or branched. Thus, in the case of a randomly branched PEI, although there are branches of different length and branches occur randomly, that molecule is a homopolymer for the purposes of the instant disclosure because that branched polymer is composed of a single monomer, ethyleneimine or aziridine. Also, one or more of the monomer or complex monomer components can be modified, substituted, derivatized and so on, for example, modified to carry a functional group. Such molecules are homopolymers for the purposes of the instant disclosure as the backbone is composed of a single simple or complex monomer.

Poorly Water Soluble Drugs

Small molecule drug candidates and drugs, as well as biological molecules, which can be modified for particular purposes or to have particular properties, may be poorly soluble or insoluble in water. Generally, the need for hydrophilicity for a molecule to survive in circulation or in tissue spaces can constrain the use of pharmacologically active hydrophobic drug candidates or drugs. Hence, development of effective formulations for poorly water soluble pharmaceutically active agents (PAA) is important in drug development and use. Current solutions include improving drug solubility or reducing drug particle size by, for example, chemical modification or physical formulation.

Chemical modification methods often involve converting the drug, e.g., by using a salt form, hydrating or attaching various water soluble functional groups, such as, amino/imino, hydroxyl, or carboxyl containing groups; water soluble polymers, such as, PEG or PEO, and the like to the original drug molecule to enhance water solubility.

Physical formulation can include using a cosolvent and/or a surfactant to dissolve a poorly soluble drug; involving a lipid or a liposome-based nanoemulsion or microemulsion; melting drug and polymer without any solvents at elevated temperatures; using a complexing agent (e.g., an inorganic salt, coordination metals (e.g., hexamine cobalt (III) chloride), chelates (e.g., EDTA, EGTA etc.), metal-olefins or metallocenes (e.g., Ferrocene), inclusion compounds (e.g., cyclodextrins, choleic acid etc.) or molecular complexes); as well as solid dispersion in a carrier, such as, e.g., acids, such as, citric acid, tartaric acid, succinic acid, HCl etc.), sugars (e.g., dextrose, sorbitol, sucrose, maltose, galactose, xylitol etc.), polymeric materials (e.g., polyvinylpyrrolidone, PEG-400, PEG-1000, PEG-4000, PEG-6000, carboxymethyl cellulose, hydroxypropyl cellulose, guar gums, xanthan gums, sodium alginates, methyl celluloses, HPMC, cyclodextrins and their derivatives, galactomannans, surfactants (e.g., polyoxyethylene stearate, a poloxamer, a deoxycholic acid, a Tween, a Span, a Gelucire, a vitamin E TPGS etc.), and the like (e.g., pentaerythritol, urea, urethane, hydroxyalkyl xanthenes etc.).

Other known strategies include drug particle size reduction, for example, micronization, which can use a milling technique, such as, use of a jet mill or a rotor stator colloid mill to reduce particle size; increase dissolution rate with increased surface area; nanosuspension, which is a submicron colloidal dispersion of pure particles of drugs, which can be stabilized by surfactants; homogenization, which often involves conventional homogenizers, sonicators and high shear fluid processors; wet milling, where the active drug is fragmented in the presence of surfactant by milling or by spraying drug dissolved in a volatile organic solvent into a heated aqueous solution; using supercritical fluids; polymorph changes; using eutectic mixtures; using self microemulsifying drug delivery systems etc.

However, those treatments may compromise pharmacologic activity.

While drugs often can be delivered through various routes, including oral, intrathecal, rectal, intranasal, subdermal, subdural, intramuscular, transdermal, topical, inhalation, injection and so on, intravenous drug delivery allows rapid and direct equilibration of the drug in the circulation, that can enable effective local concentration. A stable and controlled drug release formulation not only can avoid excessively high serum levels just after dosing but also can allow gradual release of the drug in the intravascular compartment.

Microparticles larger than 7 μm are generally cleared from the circulation by the "blood filtering organs," such as, the spleen, lungs and liver. Therefore, smaller nanoparticles, e.g., 50-500 nm, often possess longer blood circulation times.

Examples of pharmaceutically active agents (PAA), such as, drugs, include, but are not limited to, chlormethine, chlorambucil, busulfan, thiotepa, cyclophosphamide, estramustine, ifosfamide, meclilorethamine, melphalan, uramustine, lonuistine, streptozotocin, dacarbazine, procarbazine, temozolainide, cisplatin, carboplatin, oxaliplatin, satraplatin, (SP-4-3)-(cis)-aminedichloro-[2-methylpyridine]-platinum (II), methotrexate, permetrexed, raltitrexed, trimetrexate, camptothecin, camptothecin derivatives (such as, irinotecan, topotecan etc.), cladribine, chlorodeoxyadenosine, clofarabine, fludarabine, mercaptopurine, pentostatin, thioguanine, azacitidine, capecitabine, cytarabine, edatrexate, floxuridine, 5-fluorouracil, gemcitabine, troxacitabine, bleomycin, dactinomycin, adriamycin, actinomycin, mithramycin, mitomycin, mitoxantrone, porfiromycin, daunorubicin, doxorubicin, liposomal doxorubicin, epirubicin, idarubicin, valrubicin, phenesterine, tamoxifen, piposulfancamptothesin, L-asparaginase, PEG-L-asparaginase, paclitaxel, docetaxel, taxotere, vinblastine, vincristine, vindesine, vinorelbine, irinotecan, topotecan, amsacrine, etoposide, teniposide, fluoxymesterone, testolactone, bicalutamide, cyproterone, flutamide, nilutamide, aminoglutethimide, anastrozole, exemestane, formestane, letrozole, dexamethasone, prednisone, diethylstilbestrol, fulvestrant, raloxifene, toremifene, buserelin, goserelin, leuprolide, triptorelin, medroxyprogesterone acetate, megestrol acetate, levothyroxine, liothyronine, altretamine, arsenic trioxide, gallium nitrate, hydroxyurea, levamisole, mitotane, octreotide, procarbazine, suramin, thalidomide, methoxsalen, sodium porfimer, bortezomib, erlotinib hydrochloride, gefitinib, imatinib mesylate, semaxanib, adapalene, bexarotene, trans-retinoic acid, 9-cis-retinoic acid and N-(4-hydroxyphenyl) retinamide, alemtuzumab, bevacizumab, cetuximab, ibritumomab tiuxetan, rituximab, trastuzumab, gemtuzumab ozogamicin, tositumomab, interferon-α2a, interferon-α and so on, and derivatives and modifications thereof, so long as the drug, or derivative thereof, is poorly soluble or insoluble in water. Some of the molecules above are modified to be more soluble in water. For the purposes of the instant disclosure, such molecules can be modified or altered to remove such modifications resulting in a pharmaceutically active or biologically active molecule which is less hydrophilic and more hydrophobic, that is, poorly water soluble or water insoluble.

Thus, PAA's that are water insoluble or poorly water soluble, or those which are sensitive to acid environments generally cannot be conventionally administered (e.g., by intravenous injection or oral administration). In some circumstances, parenteral administration of such pharmaceuticals can be achieved by emulsification of oil-solubilized drug with an aqueous liquid (such as normal saline), often in the presence of surfactants or emulsifiers to produce an emulsion for administration.

For example, paclitaxel is a water insoluble drug. Paclitaxel is sold as Taxol® by Bristol-Myers Squibb. Paclitaxel is derived from the Pacific Yew tree, *Taxus brevifolia* (Wan et al., J. Am. Chem. Soc. 93:2325 (1971). Taxanes, including paclitaxel and docetaxel (also sold as Taxotere®) are used to treat various cancers, including, breast, ovarian and lung cancers, as well as colon, and head and neck cancers, etc.

However, the poor aqueous solubility of paclitaxel has hampered the widespread use thereof. Currently, Taxol® and generics thereof are formulated using a 1:1 solution of ethanol:Cremaphor® (polyethyoxylated castor oil) to solubilize the drug. The presence of Cremaphor® has been linked to severe hypersensitivity reactions and consequently requires medication of patients with corticosteroids (e.g., dexamethasone) and antihistamines.

Alternatively, conjugated paclitaxel, for example, Abraxane®, which is produced by mixing paclitaxel with human serum albumin, has eliminated the need for corticosteroids and antihistamine injections. However, Abraxane® generates undesirable side effects, such as, severe cardiovascular events, including chest pain, cardiac arrest, supraventricular tachycardia, edema, thrombosis, pulmonary thromboembolism, pulmonary emboli, hypertension etc, which prevents patients with high cardiovascular risk from using the drug.

Delivery of Poorly Water Soluble Drugs with Surface Modified Branched Polymers

Although branched polymers, including SBP's and ABP's, have been used for drug delivery, those attempts are primarily focused on the chemical attachment of the drug to the polymer, or physical encapsulation of such drugs in the interior through unimolecular encapsulation (U.S. Pat. Nos. 5,773,527; 5,631,329; 5,919,442; and 6,716,450).

For example, dendrimers and dendrigrafts are believed to physically entrap bioactive molecules using unimolecular encapsulation approaches, as described in U.S. Pat. Nos. 5,338,532; 5,527,524; and 5,714,166 for dense star polymers, and U.S. Pat. No. 5,919,442 for hyper comb branched polymers. Similarly, the unimolecular encapsulation of various drugs using SBP's to form a, "dendrimer box," was reported in Tomalia et al., Angew. Chem. Int. Ed. Engl., 1990, 29, 138, and in "Dendrimers and Other Dendritic Polymers", edited by Frechet & Tomalia, John Wiley & Sons, Ltd., 2001, 387-424.

Branched core shell polymers with a hydrophobic core and a hydrophilic shell may be used to entrap a poorly water soluble drug through molecular encapsulation. Randomly branched and hyperbranched core shell structures with a hydrophilic core and a hydrophobic shell have also been used to carry a drug through unimolecular encapsulation and pre-formed nanomicelles (U.S. Pat. No. 6,716,450 and Liu et al., Biomaterials 2010, 10, 1334-1341). However, those unimolecular and pre-formed micelle structures are generated in the absence of a drug.

Block copolymers, such as miktoarm polymers (i.e., Y shape/AB2 type star polymers) and linear (A)-dendritic (B) block copolymers, were observed to form sterocomplexes with paclitaxel (Nederberg et al., Biomacromolecules 2009, 10, 1460-1468 and Luo et al., Bioconjugate Chem. 2010, 21, 1216). Those block copolymers closely resemble traditional lipid or AB-type linear block copolymers, which are well known surfactants used for the generation of micelles.

However, such branched block copolymers are difficult to make and thus, are not suitable for mass production.

There are no descriptions of modifying branched homopolymers, which on exposure to a poorly soluble or water insoluble drug, spontaneously form stable aggregates which are suitable for controlled drug delivery.

SUMMARY

In one aspect, the present disclosure is directed to use of modified branched polymers (MBP) to increase the solubility of water insoluble or poorly water soluble pharmaceutically active agents (PAA), such as, drugs. Such MBP's can include both symmetrically and asymmetrically branched polymers.

In another aspect of the disclosure, the symmetrically branched polymer (SBP) has regular symmetrical branches within the polymer. In another aspect of the disclosure, the asymmetrically branched polymer (ABP) has either random or regular, asymmetrical branches. The random ABP can also have a mixture of terminal and chain branching patterns.

In another aspect of the disclosure, both ABP's and SBP's can be modified further with at least one molecule or group capable of forming additional branches at a given time so that new material properties can be achieved, wherein additional functional groups may be further attached. All of the modified polymers can be defined as modified symmetrically or asymmetrically branched polymers.

In another aspect of the disclosure, the unmodified and modified branched polymers either can be produced by a divergent or a convergent method, and either a stepwise or a one-step synthetic process can be used.

In another aspect of the disclosure, the SBP includes, but is not limited to, polyamidoamine dendrimers; polyethyleneimine dendrimers; polypropyleneimine dendrimers; polyether dendrimers; polyester dendrimers; comb branched/star branched polymers, such as, polyamidoamine, polyethyleneoxide (PEO), polyethyleneglycol (PEG), polymethyloxazoline, polyethyloxazoline, polymethylmethacrylate (PMA), polystyrene, polybutadiene, polyisoprene and polydimethylsiloxane; comb branched dendrigrafts, such as, polyethyloxazoline, polymethyloxazoline, polyethyleneimine, polyamidoamine; and so on.

In a further aspect of the disclosure, the SBP can have an interior void space, while the ABP can have unevenly distributed void spaces.

In another aspect of the disclosure, a hybrid branched polymer comprising the aforementioned SBP's, such as, dendrimers or dendrigrafts, and ABP's, such as, regular and randomly branched polymers, as well as star branched and comb branched polymers, or combination thereof, can also be used for the generation of said drug-induced aggregates or nanoparticles of interest.

In another aspect of the disclosure, the branched polymers are modified with functional groups, such as, but not limited to, $NH_2$, NHR, $NR_2$, $NR_3^+$, COOR, COOH, $COO^-$, OH, C(O)R, $C(O)NH_2$, C(O)NHR or $C(O)NR_2$, wherein R can be any aliphatic group, aromatic group or combination thereof; an aliphatic group (e.g., a hydrocarbon chain), which can be branched, can contain one or more double and/or triple bonds and/or may be substituted; an aromatic group, which may contain a plurality of rings, which may be fused or separated, the rings may be of varying size and/or may contain substituents; perfluorocarbon chains; saccharides and/or polysaccharides, which may be of varying ring sizes, the rings may contain a heteroatom, such as a sulfur or a nitrogen atom, may be substituted, may contain more than one species of saccharide, may be branched and/or may be substituted; polyethylene glycols; and the like.

The molecular weight of the MBP's can range from about 500 to over 5,000,000; from about 500 to about 1,000,000; from about 1,000 to about 500,000; or from about 2,000 to about 100,000.

In another aspect of the disclosure, the surface of the symmetrically and asymmetrically polymers is modified so that the physical properties of the surface groups will be more compatible with a PAA of interest, thus making the PAA more miscible with the surface group region/domain of the MBP's.

In an embodiment, the modification of branched polymers is with hydrophobic functional groups, such as, aliphatic chains (e.g., hydrocarbon chains comprising 1 to about 22 carbons, whether linear or branched), aromatic structures (e.g. containing one or more aromatic rings, which may be fused) or combinations thereof.

In contrast to known drug carriers, the PAA's of the instant disclosure are not physically entrapped within said branched polymer structures. Instead, the PAA either can be located at or dispersed in the domains/regions containing surface functional groups of each branched polymer.

The resulting structures of interest optionally can be preserved, for example, by lyophilization or other form of desiccation, which may further stabilize the structures of interest. Once redissolved in water or a buffer, nanoparticles with sizes ranging from about 50 to about 500 nm in diameter can be obtained.

The presence of multiple, often functionalized branches enables the formation of intramolecular and intermolecular crosslinks, which may stabilize the PAA-containing nanoparticles. On dilution, said physical aggregate or nanoparticle deconstructs releasing drug at a controlled rate.

In another aspect of the disclosure, the branched polymer can comprise targeting moieties/groups including, but not limited to, an antibody or antigen-binding portion thereof, antigen, cognate carbohydrates (e.g., sialic acid), a cell surface receptor ligand, a moiety bound by a cell surface receptor, a moiety that binds a cell surface saccharide, an extracellular matrix ligand, a cytosolic receptor ligand, a growth factor, a cytokine, an incretin, a hormone, a lectin, a lectin ligand, such as, a galactose, a galactose derivative, an N-acetylgalactosamine, a mannose, a mannose derivative and the like, a vitamin, such as, a folate or a biotin, avidin, streptavidin, neutravidin, DNA, RNA etc. Such targeted nanoparticles release drug at the preferred treatment locations, and therefore, enhance local effective concentrations and can minimize undesired side effects.

In another aspect of the disclosure, a targeting moiety/ group and a functional group, including, hydrophobic, hydrophilic and/or ionic functional groups, are attached to the branched polymer prior to the formation of the composite nanoparticle for targeted drug delivery.

In another aspect of the disclosure, a diagnostic agent, such as, a contrast reagent, also can be carried by said structures of interest, for example, for in vivo imaging. In an embodiment, the diagnostic agent is one which is poorly soluble or insoluble in water, thereby negating a need for a drug to form a structure of interest.

In some embodiments, an imaging agent is one comprising a metal or is paramagnetic, e.g., magnetic resonance imaging materials, which can be deposited or entrapped within said branched polymer of said nanocomposite-based particle.

In yet another aspect of the disclosure, the diagnostic material containing nanoparticles can further comprise a targeting moiety/group, which allows such nanoparticle to target specific locations for diagnosis.

In other embodiments, a structure of interest comprises a second or more PAA's. The second or more PAA's may or may not be poorly soluble or insoluble in water.

In another aspect of disclosure, the nanoparticle can carry plural similar PAA's or can carry PAA's of different function or activity, such as, types of drugs to form a combination or cocktail therapy. Such drugs may include, but are not limited to, small molecule drugs, inorganic drugs and biological molecule-based drugs, such as peptides, proteins, antibodies or antigen-binding portions thereof, enzymes, vaccines and so on, for the treatment of various diseases or general use, such as, for cosmetics and over the counter products.

In another aspect of the disclosure, the nanoparticle-based drug formulations also can be used in drug discovery and development, where various therapeutic formulations can be screened and tested rapidly.

Additional features and advantages of the present disclosure are described in, and will be apparent from, the following Detailed Description and the attached Figures.

BRIEF DESCRIPTION OF THE FIGURES

The following description of the figures and the respective drawings are non-limiting examples that depict various embodiments that exemplify the present disclosure.

FIGS. 1A-D depict SBP's including a dendrimer (FIG. 1A), a star shaped polymer (FIG. 1D), a dendrigraft (FIG. 1B) and a comb shaped polymer (FIG. 1C). All have a core, whether globular or linear.

FIG. 6A presents chemical modification reactions of random asymmetrically branched PEI homopolymers. FIG. 6B depicts a one-pot synthesis of hydrophobically modified, randomly branched poly(2-ethyloxazoline) with a primary amino group at the focal point of the polymer. The initiator/surface group (I) is the brominated hydrocarbon. The reaction opens the oxazoline ring.

" FIG. 10A depicts a symmetrically branched polymer and FIG. 10B depicts an asymmetrically branched polymer.

FIG. 11A depicts a symmetrically branched polymer and FIG. 11B depicts an asymmetrically branched polymer.

FIG. 12A depicts a symmetrically branched polymer and FIG. 12B depicts an asymmetrically branched polymer.

DETAILED DESCRIPTION OF THE DISCLOSURE

Figures 2A, 2B:
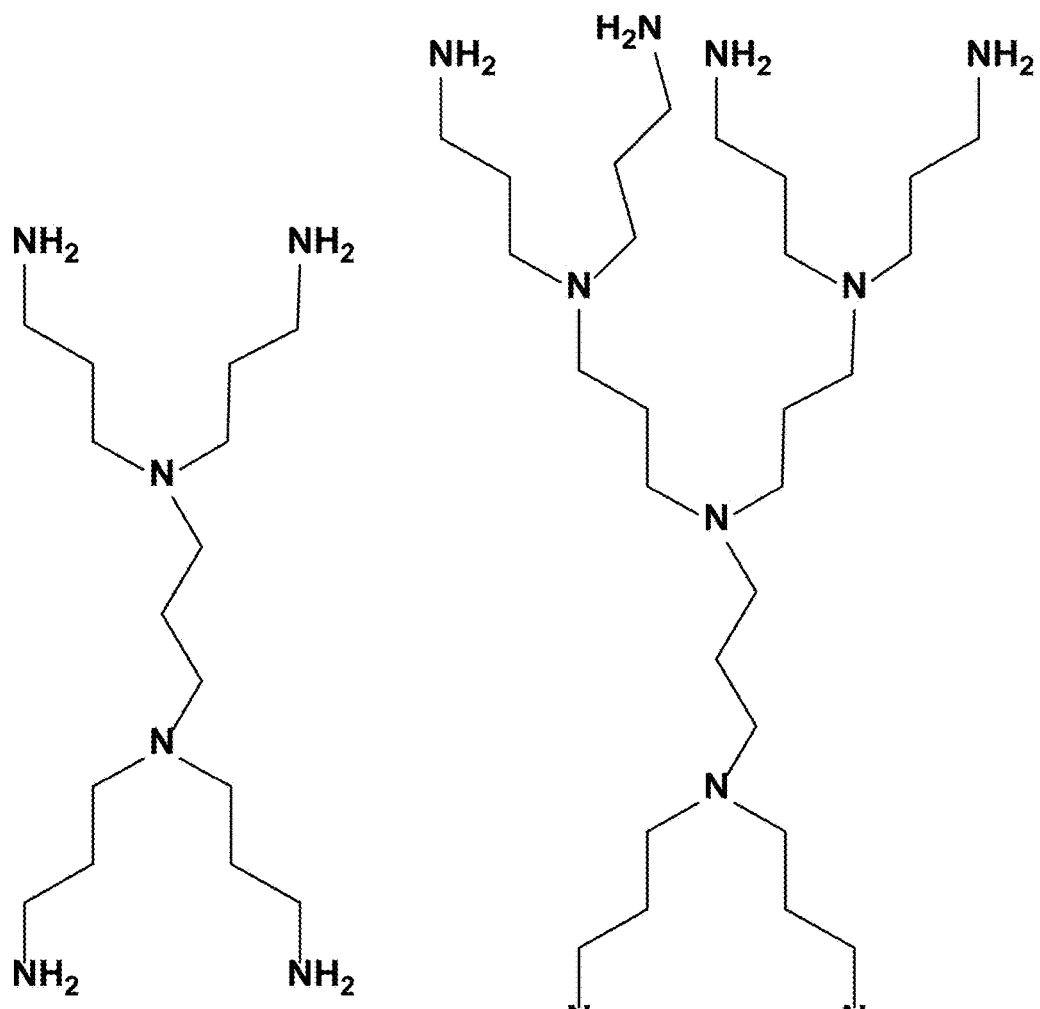
FIGS. 2A and 2B depict chemical structures of symmetrically branched PPI dendrimers.
Figure 3:
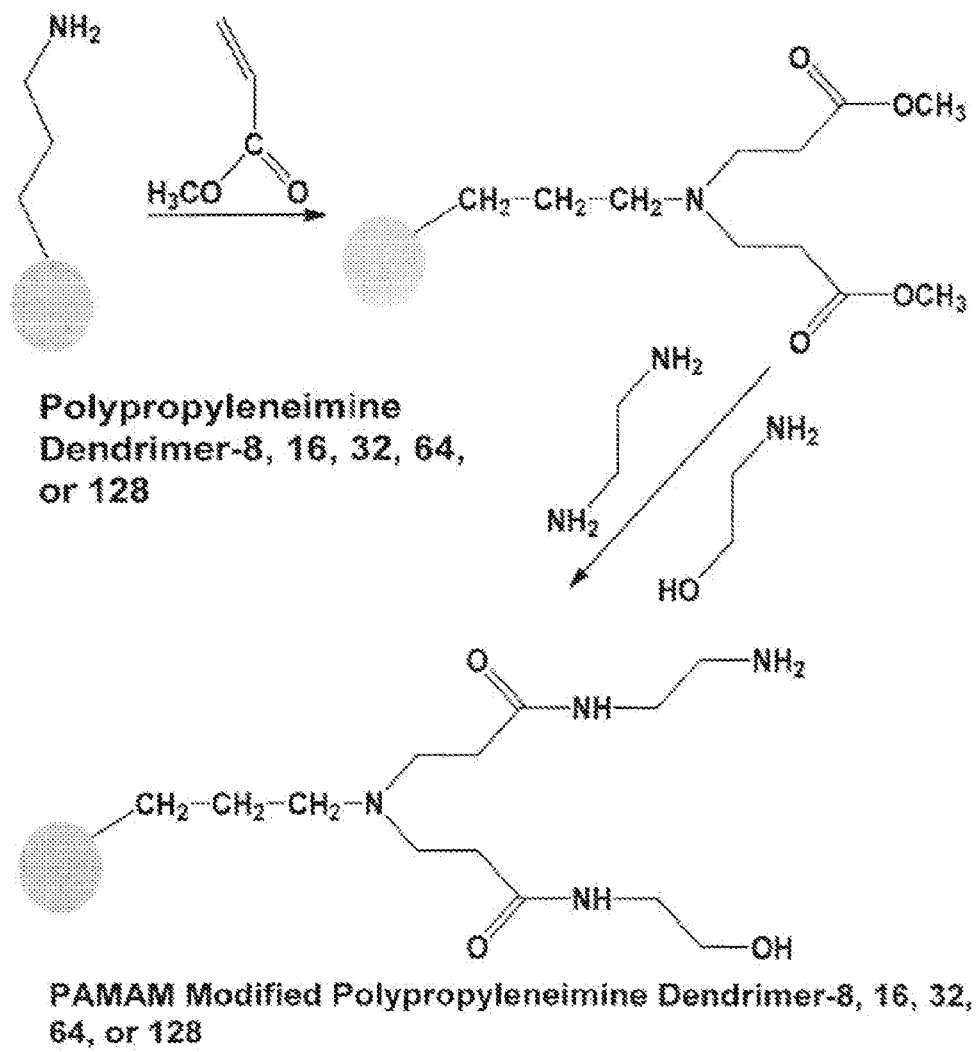
FIG. 3 depicts chemical modification reactions of symmetrically branched PPI dendrimers. The numbers, 8, 16, 32 and so on indicate the number of reactive groups at the surface of the dendrimer.

The drug solubility in this disclosure is defined as, relative to parts of solvent required to solubilize for one part of drug, <30 (soluble), 30-100 (poorly soluble) and >100 (insoluble).

For the purposes of the instant disclosure, the words, such as, "about," "substantially" and the like are defined as a range of values no greater than 20% from the stated value or figure. "Homopolymer," is as described hereinabove.

Drugs of Interest

The PAA described in this disclosure includes any chemical/small molecule-based drug, inorganic-based drug, biological/large molecule-based drug, modifications and/or derivatives thereof, and combinations thereof, wherein the drug is poorly soluble or insoluble in water. Hence, a drug of interest can be a small molecule, a salt thereof in which the molecule is modified to be water insoluble or poorly water soluble or can be a biological molecule which is modified to be water insoluble or poorly water soluble.

Chemical/small molecule drugs can include any substantially poorly soluble or water insoluble pharmacologically active agents contemplated for use in the practice of the present disclosure include PAA's, drugs, imaging agents, diagnostic agents, agents of nutritional value, supplements, vitamins, lifestyle chemicals and the like. Some of those may need to be converted to a less water soluble form, for example, changing the PAA from a salt to a non-salt form or from a charged to a non-charged molecule.

Suitable examples of PAA's include drugs which are poorly soluble or insoluble in water, which include, growth agents, AIDS adjunct agents, alcohol abuse preparations, such as, agents for treating dependence or withdrawal, Alzheimer's Disease treatments, Amyotrophic Lateral Sclerosis treatments, analgesics, anesthetics, anticonvulsants, antidiabetic agents, antidotes, antifibrosis therapies, antihistamines, anti-infective agents, such as, antibiotics, antivirals, antifungals, amebicides, antihelmintics, antimalarials, leprostatics and so on, antineoplastics, antiparkinsonian agents, antirheumatic agents, appetite stimulants, biological response modifiers, biologicals, blood modifiers, such as, anticoagulants, colony stimulating factors, hemostatics, plasma extenders, thrombin inhibitors and so on, bone metabolism regulators, cardioprotective agents, cardiovascular agents, such as, adrenergic blockers, adrenergic stimulators, ACE inhibitors, antiarrhythmics, antilipemic agents, calcium channel blockers, diuretics, vasopressors and so on, CNS stimulants, cholinesterase inhibitors, contraceptives, fertility treatments, ovulation stimulators, cystic fibrosis managements agents, detoxifying agents, diagnostics, dietary supplements, dopamine receptor agonists, endometriosis management agents, enzymes, erectile dysfunction treatments, foot care products, GI agents, such as antacids, antidiarrheals, antiemetics, antiflatulants, bowel evacuants, digestive enzymes, histamine receptor agonists, laxatives, proton pump inhibitors, prostaglandins and so on, Gaucher's Disease treatments, gout treatments, homeopathic remedies, skin treatments, vitamins, nutrients, hormones, hypercalcemia management treatments, hypocalcemia management treatments, immunomodulators, immunosuppressants, levocarnitine deficiency treatments, mast cell stabilizers, migraine treatments, motion sickness products, such as, benadryl and phenergan, decongestants, antihistamines, cough suppressants, multiple sclerosis treatments, muscle relaxants, nasal preparations, such as, antiinflammatories, smoking cessation aids, appetite suppressants, nucleoside analogs, obesity managements, ophthalmic preparations, such as, antibiotics, antiglaucoma agents, artificial tears, lubricants and so on, sexual aids, lubricants, osteoporosis treatments, otic preparations, such as, antiinfectives and cerumenolytics, minerals, oxytocics, parasympatholytics, parasympathomimetics, patent ductus arteriosus agents, phosphate binders, *porphyria* agents, prostaglandins, psychotherapeutic agents, radiopaque agents, respiratory agents, such as, antiinflammatories, antitussives, bronchodilators, decongestants, expectorants, leukotrienes antagonists, surfactants and so on, salt substitutes, sedatives, hypnotics, skin and mucous membrane preparations, such as, acne treatments, anorectal treatments, such as, hemorrhoid treatments and enemas, antiperspirants, antipruritics, antipsoriatic agents, antiseborrheic agents, burn treatments, cleansing agents, depigmenting agents, emollients, hair growth retardants, hair growth stimulators, keratolytics, hair problem treatments, mouth and throat problem treatments, shampoos, photosensitizing agents, wart treatments, wound care treatments and so on, over the counter pharmaceutics and products, such as, deodorants, Tourette's Syndrome agents, tremor treatments, urinary tract agents, such as, acidifiers, alkalinizers, antispasmodics, benign prostatic hyperplasia treatments, calcium oxalate stone preventors, enuresis management agents and so on, vaginal preparations, such as, antiinfectives, hormones and so on, vasodilators, vertigo treatments, Wilson's Disease treatments and so on.

Listed herein are drugs of interest as well as forms of drugs which may be modified, for example, as salts. For the purposes of the invention, any such ionized or hydrophilic forms are modified as known in the art to remove such functional groups, modifications and the like to yield nonmodified or other forms of drugs which are poorly soluble or not soluble in water. Examples of pharmaceutically active agents, drugs and the like include those listed herein and, for example, analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate and the like); anesthetics (e.g., cyclopropane, enflurane, halothane, isoflurane, methoxyflurane, nitrous oxide, propofol and the like); antiasthmatics (e.g., azelastine, ketotifen, traxanox, amlexanox, cromolyn, ibudilast, montelukast, nedocromil, oxatomide, pranlukast, seratrodast, suplatast tosylate, tiaramide, zafirlukast, zileuton, beclomethasone, budesonide, dexamethasone, flunisolide, triamcinolone acetonide and the like); antibiotics (e.g., neomycin, streptomycin, chloramphenicol, cephalosporin, ampicillin, penicillin, tetracycline and the like); antidepressants (e.g., nefopam, oxypertine, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, trimipramine maleate, protriptyline hydrochloride and the like); antidiabetics (e.g., biguanides, hormones, sulfonylurea derivatives, and the like); antifungal agents (e.g., griseofulvin, ketoconazole, amphotericin B, nystatin, candicidin and the like); antihypertensive agents (e.g., propanolol, propafenone, oxyprenolol, nifedipine, reserpine, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine and the like); anti-inflammatories (e.g., non-steroidal compounds, such as, indomethacin, naproxen, ibuprofen, ramifenazone, piroxicam and so on, and steroidal compounds, such as, cortisone, dexamethasone, fluazacort, hydrocortisone, prednisolone, prednisone and the like); antineoplastics (e.g., adriamycin, cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, Taxol and derivatives thereof, taxotere and derivatives thereof, vinblastine, vincristine, tamoxifen, etoposide, piposulfan and the like); antianxiety agents (e.g., lorazepam, buspirone hydrochloride, prazepam, chlordiazepoxide hydrochloride, oxazepam, clorazepate dipotassium, diazepam, hydroxyzine pamoate, hydroxyzine hydrochloride, alprazolam, droperidol, halazepam, chlormezanone, dantrolene and the like); immunosuppressive agents (e.g., cyclosporine, azathioprine, mizoribine, FK506 (tacrolimus) and the like); antimigraine agents (e.g., ergotamine tartrate, propanolol hydrochloride, isometheptene mucate, dichloralphenazone and the like); sedatives/hypnotics (e.g., barbiturates (e.g., pentobarbital, pentobarbital sodium, secobarbital sodium and the like) or benzodiazapines (e.g., flurazepam hydrochloride, triazolam, tomazeparm, midazolam hydrochloride and the like); antianginal agents (e.g., β-adrenergic blockers, calcium channel blockers (e.g., nifedipine, diltiazem hydrochloride and the like) and nitrates (e.g., nitroglycerin, isosorbide dinitrate, pentaerythritol tetranitrate, erythrityl tetranitrate and the like)); antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine and the like); antimanic agents (e.g., lithium carbonate); antiarrhythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride and the like); antiarthritic agents (e.g., phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium and the like); antigout agents (e.g., colchicine, allopurinol and the like); anticoagulants (e.g., heparin, heparin sodium, warfarin sodium and the like); thrombolytic agents (e.g., urokinase, streptokinase, altoplase and the like); antifibrinolytic agents (e.g., aminocaproic acid); hemorheologic agents (e.g., pentoxifylline); antiplatelet agents (e.g., aspirin, empirin, ascriptin and the like); anticonvulsants (e.g., valproic acid, divalproate sodium, phenytoin, phenytoin sodium, clonazepam, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione and the like); antiparkinson agents (e.g., ethosuximide and the like); antihistamines/antipruritics (e.g., hydroxyzine hydrochloride, diphenhydramine hydrochloride, chlorpheniramine maleate, brompheniramine maleate, cyproheptadine hydrochloride, terfenadine, clemastine fumarate, triprolidine hydrochloride, carbinoxamine maleate, diphenylpyraline hydrochloride, phenindamine tartrate, azatadine maleate, tripelennamine hydrochloride, dexchlorpheniramine maleate, methdilazine hydrochloride, trimprazine tartrate and the like); agents useful for calcium regulation (e.g., calcitonin, parathyroid hormone and the like); antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate and the like); antiviral agents (e.g., interferon γ, zidovudine, amantadine hydrochloride, ribavirin, acyclovir and the like); antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium and the like), penicillins (e.g., ampicillin, amoxicillin, penicillin G benzathine, cyclacillin, ampicillin sodium, penicillin G K, penicillin V K, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, nafcillin sodium and the like), erythromycins (e.g., erythromycin ethylsuccinate, erythromycin, erythromycin estolate, erythromycin lactobionate, erythromycin stearate, erythromycin ethylsuccinate and the like), tetracyclines (e.g., tetracycline hydrochloride, doxycycline hyclate, minocycline hydrochloride and the like), and the like); anti-infectives (e.g., GM-CSF); bronchodilators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate); anticholinergic agents (e.g., ipratropium bromide); xanthines (e.g., aminophylline, dyphylline, metaproterenol sulfate, aminophylline); mast cell stabilizers (e.g., cromolyn sodium); inhalant corticosteroids (e.g., flunisolide, beclomethasone dipropionate monohydrate and the like), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide and the like); hormones (e.g., androgens (e.g., danazol, testosterone cypionate, fluoxymesterone, ethyltostosterone, testosterone enanthate, methyltestosterone, fluoxymesterone, testosterone cypionate and the like); estrogens (e.g., estradiol, estropipate, conjugated estrogens and the like), progestins (e.g., methoxyprogesterone acetate, norethindrone acetate and the like), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate and the like), thyroid hormones (e.g., levothyroxine sodium); and the like); and the like; hypoglycemic agents (e.g., human insulin, purified beef insulin, purified pork insulin, glyburide, chlorpropamide, glipizide, tolbutamide, tolazamide and the like); hypolipidemic agents (e.g., clofibrate, dextrothyroxine sodium, probucol, lovastatin, niacin and the like); proteins (e.g., DNase, alginase, superoxide dismutase, lipase and the like); nucleic acids (e.g., sense or anti-sense nucleic acids encoding any therapeutically useful protein, including any of the proteins described herein and the like); agents useful for erythropoiesis (e.g., erythropoietin); antiulcer or antireflux agents (e.g., famotidine, cimetidine, ranitidine hydrochloride and the like); antinauseants or antiemetics (e.g., meclizine hydrochloride, nabilone, prochlorperazine, dimenhydrinate, promethazine hydrochloride, thiethylperazine, scopolamine and the like); oil-soluble vitamins (e.g., vitamins A, D, E, K and the like); and as well as other drugs such as mitotane, visadine, halonitrosoureas, anthrocyclines, ellipticine and the like.

Examples of diagnostic agents contemplated for use in the practice of the present disclosure include, but are not limited to, for example, magnetic resonance imaging contrast agents (e.g., various metal ions, such as, gadolinium based compounds for functional MRI, fluorocarbons, lipid soluble paramagnetic compounds and the like), ultrasound contrast agents, radiocontrast agents, such as, conventional radionuclides, such as, iodine, copper, fluorine, gallium, thallium and the like, which may be complexed with a carrier (e.g., iodo-octanes, halocarbons, renografin and the like), as well as other diagnostic agents which cannot readily be delivered without some physical and/or chemical modification to accommodate the substantially water insoluble nature thereof. Metals and radionuclides can be carried or bound to a protein, lipid, nucleic acid, chelator, such as a small molecule, or combinations thereof.

Examples of agents of nutritional or lifestyle value contemplated for use in the practice of the present disclosure include amino acids, sugars, lipids, proteins, carbohydrates, oils, such as, fish oil, fat-soluble vitamins (e.g., vitamins A, D, E, K and the like), minerals, supplements, fats, emollients, tanning agents, moisturizers and the like, or combinations thereof.

Nanocomposite or Nanoaggregate

A nanocomposite is a physical mixture of two or more materials or components (e.g., polymer and PAA molecules). In the instant disclosure, such a mixture could contain different nanoscopic phases or domains formed between the PAA and branched homopolymer molecule in either solid or liquid states. Nanocomposite can include a combination of a bulk matrix (e.g., branched homopolymers and PAA's) and nanodimensional phase(s), which may exhibit different properties due to dissimilarities of structure and chemistry (e.g., the domain formed by the PAA and the surface groups of branched polymer, as well as the domains formed by the interior of the branched polymers). Since the solubility of the domains/phases may be different, on dissolving the nanocomposite in an aqueous solution, one of the phases may dissolve faster than the other or others, resulting in a gradual breakdown of the composite aggregate resulting in a graded and controlled release of the composite components and optionally, reformation of one or more of the components into a novel form, such as, a new aggregate.

The size of the aggregates described in the disclosure ranges from between about 10 to about 500 nm in diameter, or from about 30 nm to about 300 nm in diameter. Aggregates may exhibit size-related properties that differ significantly from those observed for microparticles or bulk materials.

SBP's are depicted in FIG. 1, with symmetric branches, wherein all the homopolymers of interest possess a core and exhibit symmetric branch junctures consisting of either of terminal or chain branches throughout the homopolymer. The functional groups are present predominantly at the exterior.

The modified SBP's can be obtained, for example, through chemically linking functional groups on, for example, symmetrically branched PAMAM or PPI dendrimers, commercially available from Aldrich, polyether dendrimers, polyester dendrimers, comb branched/star branched polymers, such as, those containing PEO, PEG, PMOX or PEOX, polystyrene, and comb branched dendrigrafts, such as, those containing PEOX, PMOX or PEI.

The synthetic procedures for making such SBP's/dendrimers are known (see, for example, "Dendrimers and Other Dendritic Polymers," Frechet & Tomalia, eds., John Wiley & Sons, Ltd., 2001) using commercially available reagents (for example, various generations of PPI dendrimers, FIG. 2) or a number of SBP's are commercially available. The synthesis of comb branched and combburst polymers is known (see, for example, U.S. Pat. Nos. 5,773,527; 5,631,329; and 5,919,442).

The higher branching densities of SBP's render the polymers molecularly compact with a well defined interior void space, which makes such molecules suitable as a carrier for entities, such as, reporters or PAA's entrapped or encased therein.

The surface modifications can enhance the properties and uses of the resulting modified SBP's. For example, with suitable modification, a water insoluble SBP can become water soluble, while an SBP with a high charge density can be modified to carry very low or no charge on the polymer or at the polymer surface. On the other hand, a water soluble SBP can be modified with hydrophobic surface groups to enhance the ability to solubilize water insoluble or poorly water soluble drugs at the surface thereof.

In one embodiment of the instant disclosure, the SBP (for example, either a symmetrically branched PEI dendrimer, a PPI dendrimer, a PAMAM dendrimer or a symmetrically branched PEI dendrigraft) can be modified with different kinds of, for example, primary amine groups through, for example, Michael addition or an addition of acrylic esters onto amine groups of the homopolymer. Thus, for example, through a Michael addition reaction, methyl acrylate can be introduced onto the primary and/or secondary amino groups of PEI, PPI and polylysine (PLL) homopolymers. The ester groups then can be further derivatized, for example, by an amidation reaction. Thus, for example, such an amidation reaction with, for example, ethylenediamine, can yield the addition of an amino group at the terminus of the newly formed branch. Other modifications to the homopolymer can be made using known chemistries, for example, as provided in, "Poly(amines) and Poly(ammonium salts)" in Handbook of Polymer Synthesis (Part A), Kricheldorf, ed., New York, Marcel Dekker, 1994; and "Dendrimers and Other Dendritic Polymers," Frechet & Tomalia, eds., John Wiley & Sons, Ltd., 2001.

On such addition, a modified SBP, such as, a modified PEI, PPI, PAMAM dendrimer or PEI dendrigraft, is formed. As an extension of the SBP, such as PPI and PEI, the resulting modified SBP also is symmetrically branched. Depending on the solvent environment (i.e. pH or polarity), the surface functional groups can carry different charge and/or charge density, and/or hydrophobic groups. The molecular shape and surface functional group locations (i.e., surface functional group back folding) then can be tuned further, based on those characteristic properties.

In another embodiment of the disclosure, the modified SBP's can be produced using any of a variety of synthetic schemes that, for example, are known to be amenable to reaction with a suitable site on the homopolymer. Moreover, any of a variety of reagents can be used in a synthetic scheme of choice to yield any of a variety of modifications or additions to the homopolymer backbone. Thus, for example, in the case of the Michael addition reaction to an amine described above, the addition of any of a variety of substituents can be used, for example, at the alkylation stage, using for example, any of a variety of acrylate reagents, such as, an acrylate comprising a hydrocarbon substituent, such as saturated or unsaturated hydrocarbons comprising 1 to about 22 carbons, which my be substituted, aliphatic, aromatic, ringed, saturated at one or more bonds or a combination thereof. Thus, suitable reactants include, methyl acrylate, ethyl acrylate, propyl acrylate, butyl acrylate, pentyl acrylate, hexyl acrylate, heptyl acrylate, octyl acrylate, nonyl acrylate, decyl acrylate, undecyl acrylate, dodecyl acrylate and so on, and mixtures thereof. Similarly, at the amidation stage in the example exemplified above, any of a variety of amines can be used. For example, ethylenediamine, monoethanolamine, tris(hydroxymethyl)aminomethane, alkyl amine, allyl amine, or any amino modified polymer, including those comprising PEG, PEO, perfluoropolymers, polystyrene, polyethylene, polydimethylsiloxane, polyacrylate, polymethylmethacrylate and the like, and mixtures thereof, can be used.

Such a synthetic strategy would allow not only symmetric growth of the molecule, where more branches with different chemical compositions can be introduced, but also the addition of multiple functional groups at the exterior of the structure. The precursor homopolymer can be modified, and continuously, using the same or a different synthetic process until the desired SBP's with appropriate molecular weight and functional groups are attained. In addition, the hydrophobic and hydrophilic properties, as well as charge densities of such polymers, can be tailored to fit specific application needs using appropriate monomers for constructing the homopolymer and suitable modification reactions.

In another embodiment of the disclosure, if a divergent synthetic procedure is used, the chain end of symmetrically star branched or comb branched homopolymer, such as, a poly(2-substituted oxazoline), including, for example, poly (2-methyloxazoline), poly(2-ethyloxazoline), poly(2-propyloxazoline) and poly(2-butyloxazoline, etc.), PEI, PEO/glycol, polyvinylpyrrolidone, polyphosphate, polyvinyl alcohol or polystyrene, can be modified with another small molecule or polymer to generate various functional groups at the homopolymeric chain ends including a primary, secondary or tertiary amine, carboxylate, hydroxyl, aliphatic (e.g., hydrocarbon chain), aromatic, fluoroalkyl, aryl, PEG, PEO, acetate, amide and/or ester groups. Alternatively, various initiators also can be utilized so that the same type of functional groups can be introduced at the chain end if a convergent synthetic approach is utilized (Dendritic Molecules, Newkome et al., eds., VCH, Weinheim, 1996; Dendrimers and Other Dendritic Polymers, Frechet & Tomalia, eds., John Wiley & Sons, Ltd., 2001; and J. Macromol. Sci. Chem. A9(5), pp. 703-727 (1975)).

Figure 4A:
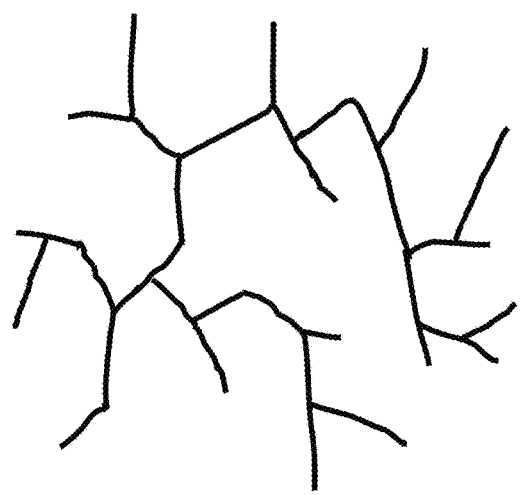
FIGS. 4A and 4B depict random (A) and regular (B) ABP's with asymmetrical branch junctures and patterns.
Figure 4B:
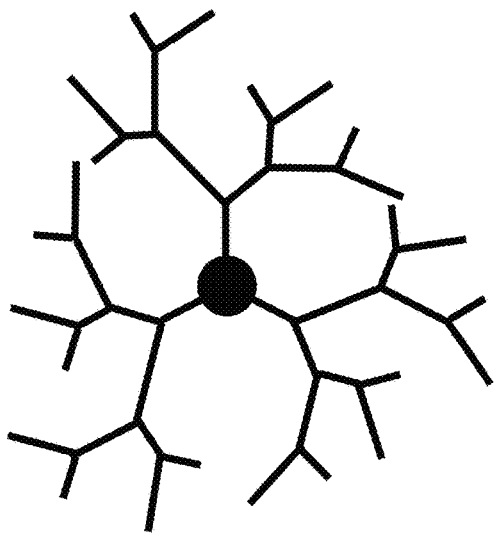
Figure 5:
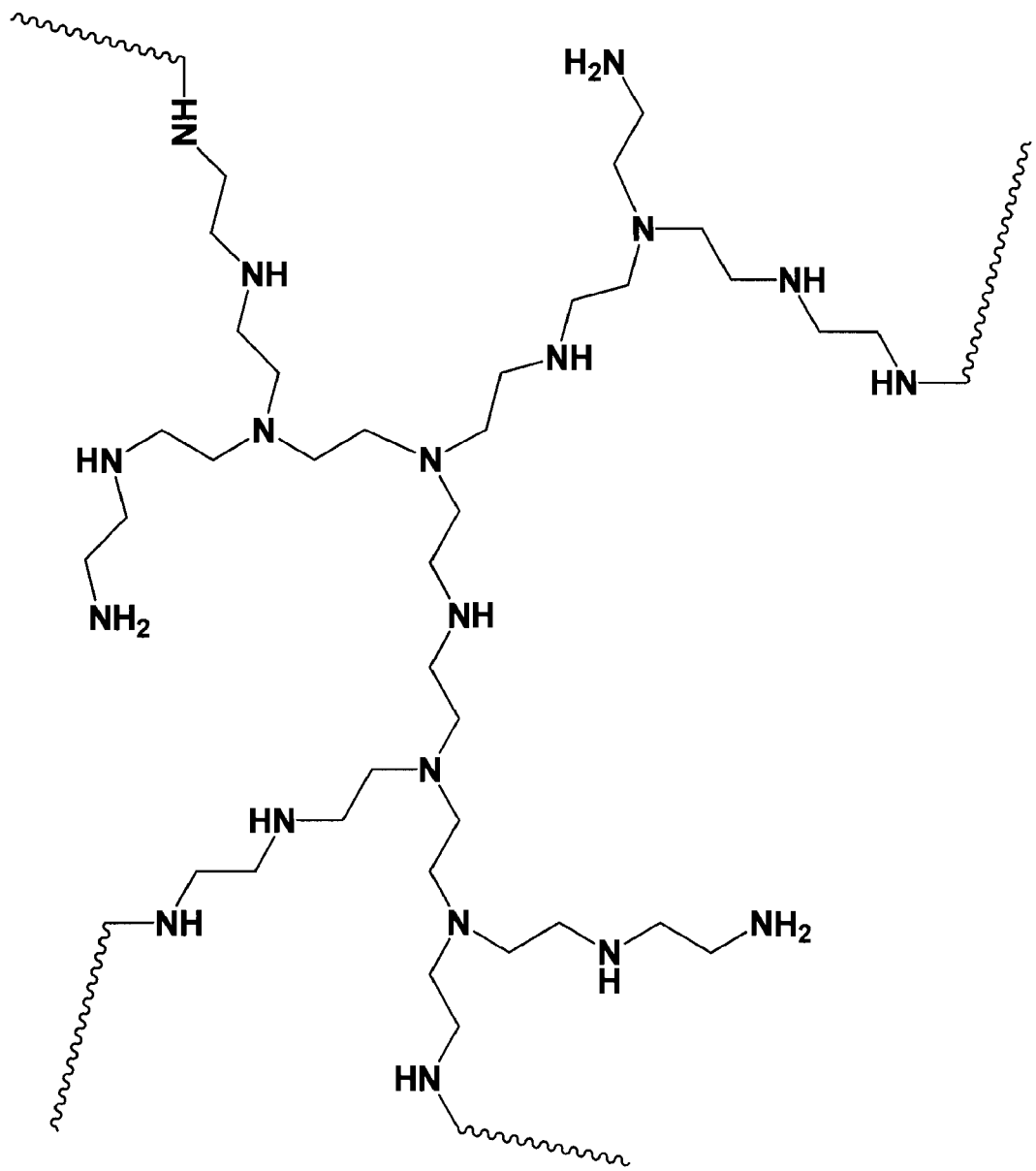
FIG. 5 depicts a chemical structure of a random asymmetrically branched PEI homopolymer.

ABP's are depicted in FIGS. 4A and 4B with asymmetric branches, wherein some of the polymers of interest possess no core and exhibit asymmetrical branch junctures consisting of both chain and terminal branches throughout the entire homopolymer. The functional groups often are present both at the exterior and in the interior. However, when a larger functional group (e.g., a large hydrophobic or hydrophilic group) is used, the functional groups often can be attached preferentially and perhaps necessarily at the exterior of the ABP, for example, possibly due to steric effects. Therefore, such surface MBP's can be utilized for solubilization of or aggregate formation with an insoluble or poorly soluble drug.

The modified ABP's can be obtained, for example, through chemically linking functional groups on regular ABP's, such as, polylysine (e.g., branched PLL), on random ABP's, such as, PEI's (commercially available from Aldrich, Polysciences, or BASF under the trade name, Luposal™) or polyoxazolines, which can be prepared according to the procedure of Litt (J. Macromol. Sci. Chem. A9(5), pp. 703-727 (1975)). Other ABP's can include, but are not limited to, polyacrylamides, polyphosphates, polyvinylpyrrolidones, polyvinyl alcohols, etc.

A variety of known starting materials can be used. For making such modified ABP's. Such monomers and polymers are available commercially in large quantities at modest cost. For example, one such precursor monomer that can be used to synthesize a homopolymer of interest is PEI. The synthesis of random asymmetrically branched PEI's is known (Jones et al., J. Org. Chem. 9, 125 (1944)). PEI's with various molecular weights are available commercially from different sources, such as, Aldrich, Polysciences and BASF (under the trade name Luposal®). The random asymmetrically branched PEI's are produced primarily through cationic ring opening polymerization of ring strained cyclic imine monomers, such as aziridines (ethyleneimine) and azetidines (propyleneimine), with Lewis or Bronsted acids as initiators. (Dermer et al., "Ethylenediamine and Other Aziridines", Academic Press, New York, (1969); and Pell, J. Chem. Soc. 71 (1959)). Since many of the methods are essentially one-pot processes, large quantities of random ABP's can be readily produced. Randomly branched poly (2-substituted oxazoline) polymers can be prepared using the procedure of Litt (J. Macromol. Sci. Chem. A9 (5), pp. 703-727 (1975)).

The synthetic processes for making ABP's often generate various branch junctures within the macromolecule. In other words, a mixture of terminal and chain branch junctures is distributed throughout the molecular structure. The branching densities of the random ABP's can be lower, and the molecular structure can be more open when compared with dendrimers and dendrigrafts. Although the branch pattern is random, the average ratio of primary, secondary and tertiary amine groups can be relatively consistent with a ratio of about 1:2:1, as described by Dick et al., J. Macromol. Sci. Chem., A4 (6), 1301-1314 (1970) and Lukovkin, Eur. Polym. J. 9, 559 (1973).

The presence of the branch junctures can make the random ABP's, such as, asymmetrically branched PEI's, form macromolecules with a possible spherical, ovoid or similar configuration. Within the globular structure, there are various sizes of pockets formed from the imperfect branch junctures at the interior of the macromolecule. Unlike dendrimers and dendrigrafts where interior pockets are always located around the center core of the molecule, the pockets of random ABP's are spread unevenly throughout the entire molecule. As a result, random ABP's possess both exterior and unevenly distributed interior functional groups that can be further reacted with a variety of molecules, thus forming new macromolecular architectures, a modified random ABP of interest.

Although having a core, the functional groups of the regular ABP are also distributed both at the exterior and in the interior, which is very similar to the random ABP. One such homopolymer is PLL, which can be made as described in U.S. Pat. Nos. 4,289,872; 4,360,646; and 4,410,688. Such homopolymers also can be modified in a manner similar as that for random ABPs, as taught herein, and as known in the art.

In one embodiment of the disclosure, the ABP (for example, either a random asymmetrically branched PEI or a regular asymmetrically branched PLL) is modified with different kinds of primary amine groups through, for example, Michael addition or an addition of acrylic esters onto amines of the polymer. Thus, for example, through a Michael addition reaction, methyl acrylate, or other acrylates as provided herein, can be introduced onto the primary and/or secondary amino groups of, for example, PEI and PLL homopolymers. The ester groups then can be further derivatized, for example, by an amidation reaction. Thus, for example, such an amidation reaction with, for example, ethylenediamine, can yield the addition of an amino group at the terminus of the newly formed branch. Other modifications to the polymer can be made using known chemistries, for example, as provided in "Poly(amines) and Poly (ammonium salts)" in "Handbook of Polymer Synthesis (Part A)," Kricheldorf, ed., New York, Marcel Dekker, 1994.

On such addition, a modified ABP, such as, a modified PEI or PLL homopolymer, is formed. As an extension of the ABP, such as PEI and PLL, the resulting modified ABP is also asymmetrically branched. Depending on the solvent environment (i.e. pH or polarity), the surface functional groups can carry different charge and charge density. The molecular shape and functional group locations (i.e., functional group back folding) then can be further tuned, based on those characteristic properties.

In another embodiment, the modified ABP's can be produced using any of a variety of synthetic schemes that, for example, are known to be amenable to reaction with a suitable site on the homopolymer. Moreover, any of a variety of reagents can be used in a synthetic scheme of choice to yield any of a variety of modifications or additions to the polymer backbone. Thus, for example, in the case of the Michael addition reaction to an amine described above, the addition of any of a variety of substituents can be used at the alkylation stage, as provided hereinabove, for example, with an acrylate, which can comprise a saturated or unsaturated hydrocarbon, such as one comprising one carbon to about 22 carbons, which may be aliphatic, branched, saturated, aromatic, ringed or combination thereof. Suitable reactants include methyl acrylate, ethyl acrylate, propyl acrylate, butyl acrylate, pentyl acrylate, hexyl acrylate, heptyl acrylate, octyl acrylate, nonyl acrylate, decyl acrylate, undecyl acrylate, dodecyl acrylate and the like, and mixtures thereof. Similarly, at the amidation stage in the example exemplified above, any of a variety of amines can be used in the methods provided herein and known in the art. For example, ethylenediamine, monoethanolamine, tris(hydroxymethyl)aminomethane, alkyl amine, allyl amine or any amino modified polymers, including polyethylene glycol (PEG), perfluoropolymers, polystyrene, polyethylene, polydimethylsilixane, polyacrylate, polymethylmethacrylate and the like, and mixtures thereof, can be used. In addition, the linking of the hydrophobic groups, including aliphatic (e.g., hydrocarbons from $C_1$ to about $C_{22}$) groups, aromatic groups, polyethylene polymers, polystyrene polymers, perfluoropolymers, polydimethylsiloxanes, polyacrylates, polymethylmethacrylates, as well as, hydrophilic groups, including a OH group, hydrophilic polymers, such as, PEOX, PEG, PEO etc. to a modified ABP can be achieved by using, for example, epoxy reactions, amidation reactions, Michael addition reactions, including using a —SH or an —NH$_2$ group reacted with maleimide, aldehyde/ketone-amine/hydrazide coupling reactions, iodo/iodoacetyl-SH coupling reactions, hydroxylamine-aldehyde/ketone coupling reactions etc. Such synthetic strategies allow not only asymmetric growth of the molecule, where more pockets are introduced, but also the addition of multiple functional groups at both the interior and the exterior of the structure. The homopolymer can be modified further using the same or a different synthetic process until the desired ABP's with appropriate molecular weight and functional groups are attained. In addition, the hydrophobic and hydrophilic properties, as well as charge density of such homopolymers, can be tailored to fit specific application needs using appropriate monomers for constructing the homopolymer and suitable modification reactions.

In another embodiment of the disclosure, a focal point (merged from various reactive chain ends during a convergent synthesis) of a random ABP, such as, polyoxazoline, can be terminated or reacted with another small molecule to generate various functional groups at the homopolymeric chain ends, including primary, secondary or tertiary amines, carboxylate, hydroxyl, alkyl, fluoroalkyl, aryl, PEG, acetate, amide and/or ester groups. Alternatively, various initiators also can be utilized so that the same type of functional group can be introduced at the surface groups where a polymerization begins during a convergent synthesis (J. Macromol. Sci. Chem. A9 (5), pp. 703-727 (1975)).

Figure 6A:
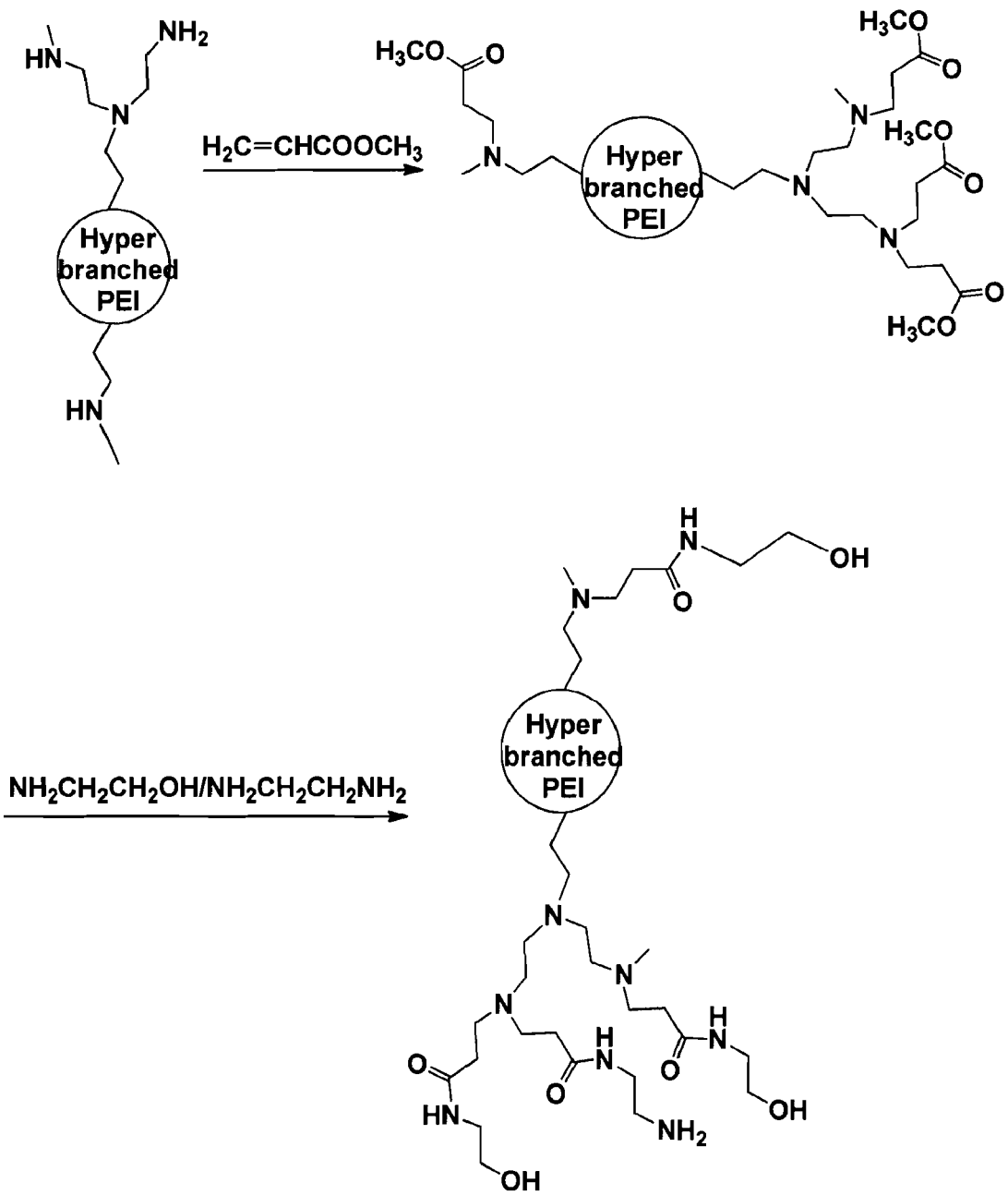
FIGS. 6A and 6B depict synthetic schemes.
Figure 6B:
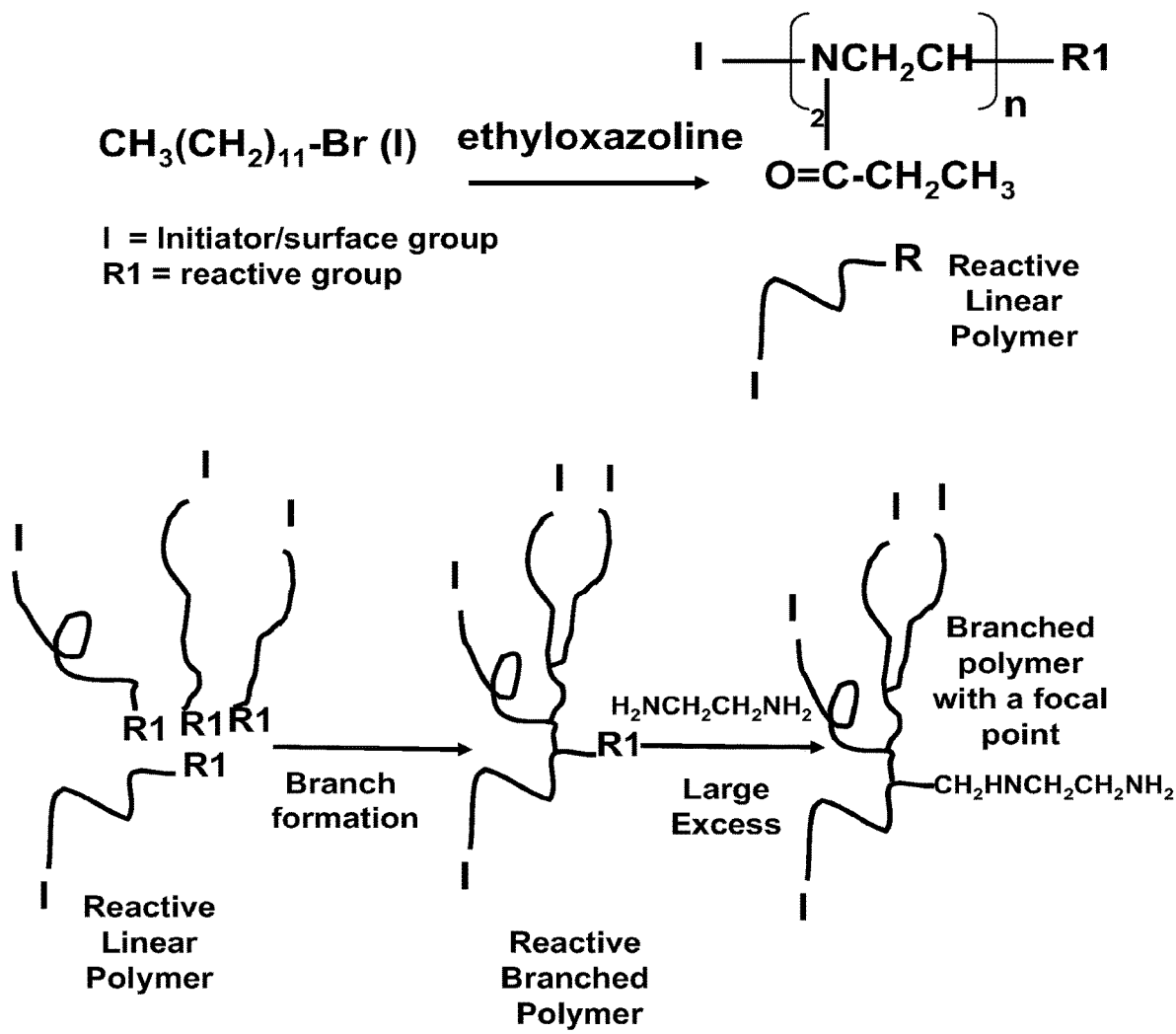
Figures 7A, 7B:
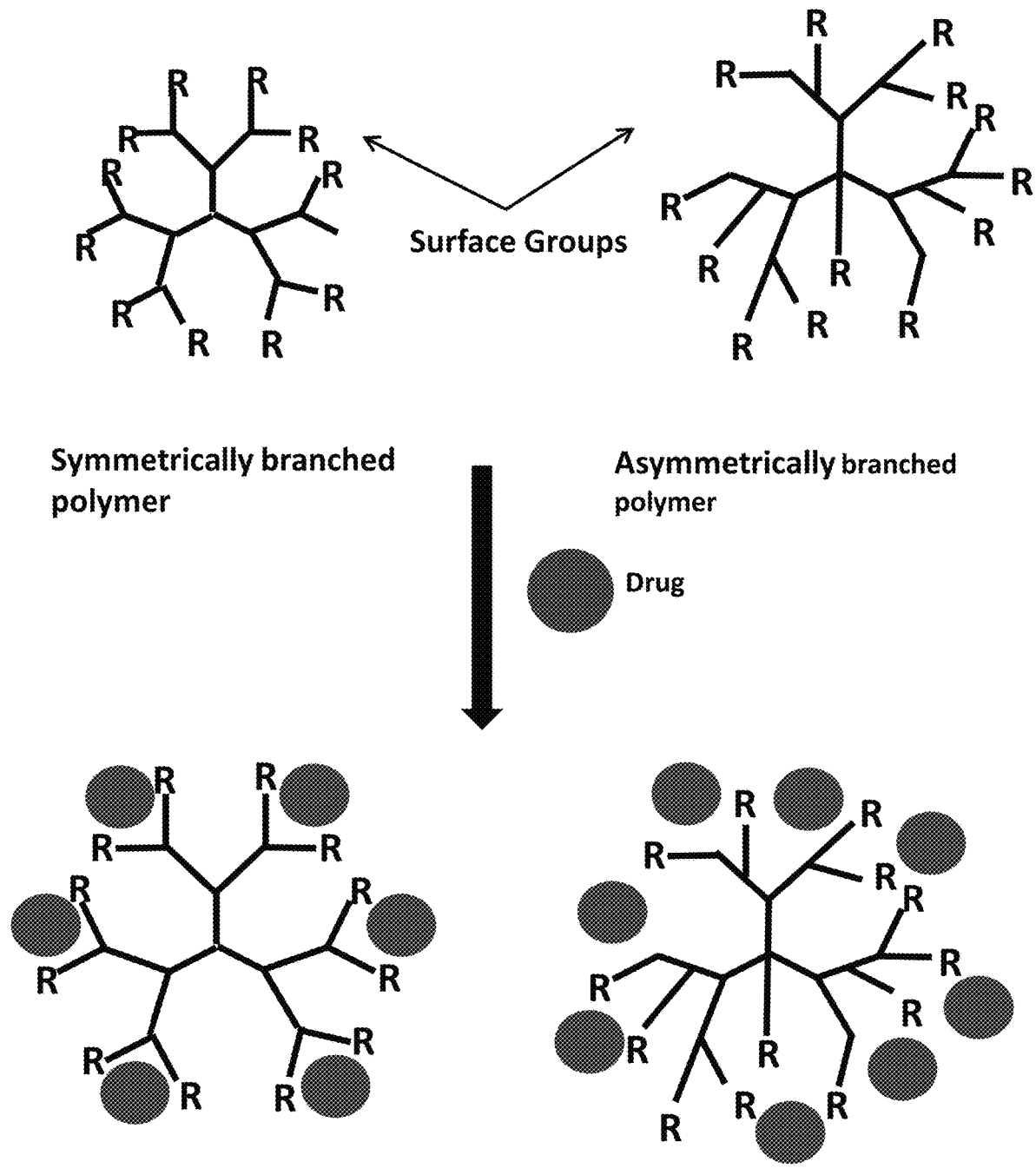
FIGS. 7A and 7B illustrate a drug loaded in or at the surface domain or region of the branched polymer (SBP's (FIG. 7A) and ABP's (FIG. 7B)). In this and other figures, R indicates a surface group and a solid circle depicts a drug of interest.
Figure 8:
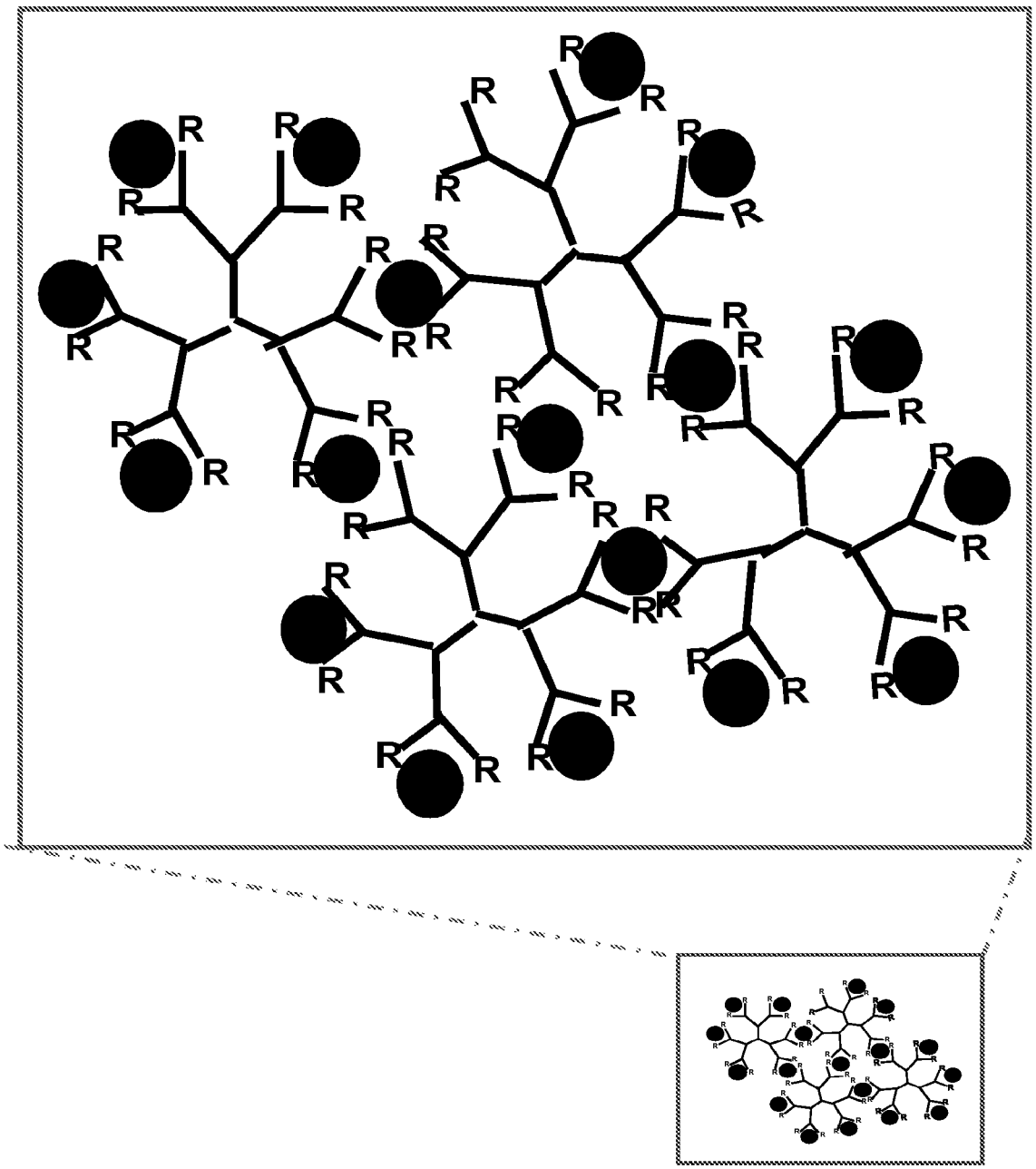
FIG. 8 illustrates one type of composite-based nanoparticles containing both drug molecules and branched polymers.
Figures 9A, 9B:
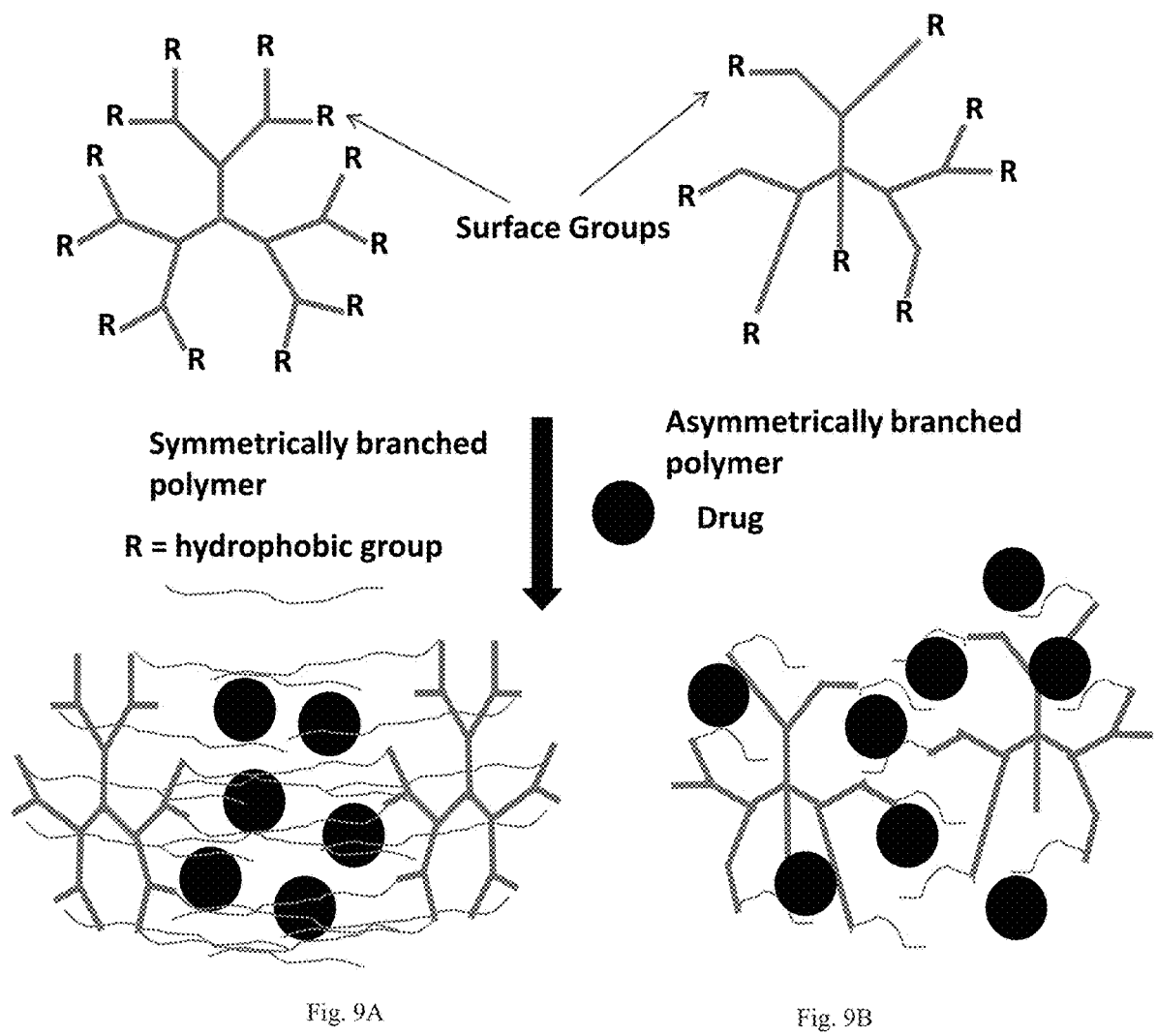
FIGS. 9A and 9B an insoluble or poorly water soluble drug that is loaded at hydrophobic surface groups of branched polymers (SBP's (FIG. 9A) and ABP's (FIG. 9B)). In this and other figures, a thin, wavy line depicts a hydrophobic surface group.

An alkyl surface modified, randomly branched poly(2-ethyloxazoline) with a primary amine group at the focal point of the branched polymer can be prepared using the Litt and Warakomski procedures, supra. For example, $CH_3(CH_2)_{17}$—Br can be utilized as an initiator for 2-ethyloxazoline polymerization through a cationic ring opening process to generate a randomly branched polymer, followed by quenching with N-tert-butyloxycarbonylpiperazine (N-Boc-piperazine) or ethylenediamine (EDA). The termination with a large excess of EDA allows the hydrophobically modified branched poly(2-ethyloxazoline) polymer to be functionalized with a primary amine group at the focal point (FIG. 6B). Alternatively, N-tert-butyloxycarbonylpiperazine (N-Boc-piperazine) terminated hydrophobically modified branched poly(2-ethyloxazoline) polymer also can be deprotected to generate a primary amino group at the focal point. If not terminated, the focal point of the polymer can be hydrolyzed to, for example, a hydroxyl group on dissolving in water (e.g., containing 1N $Na_2CO_3$).

Figure 10A:
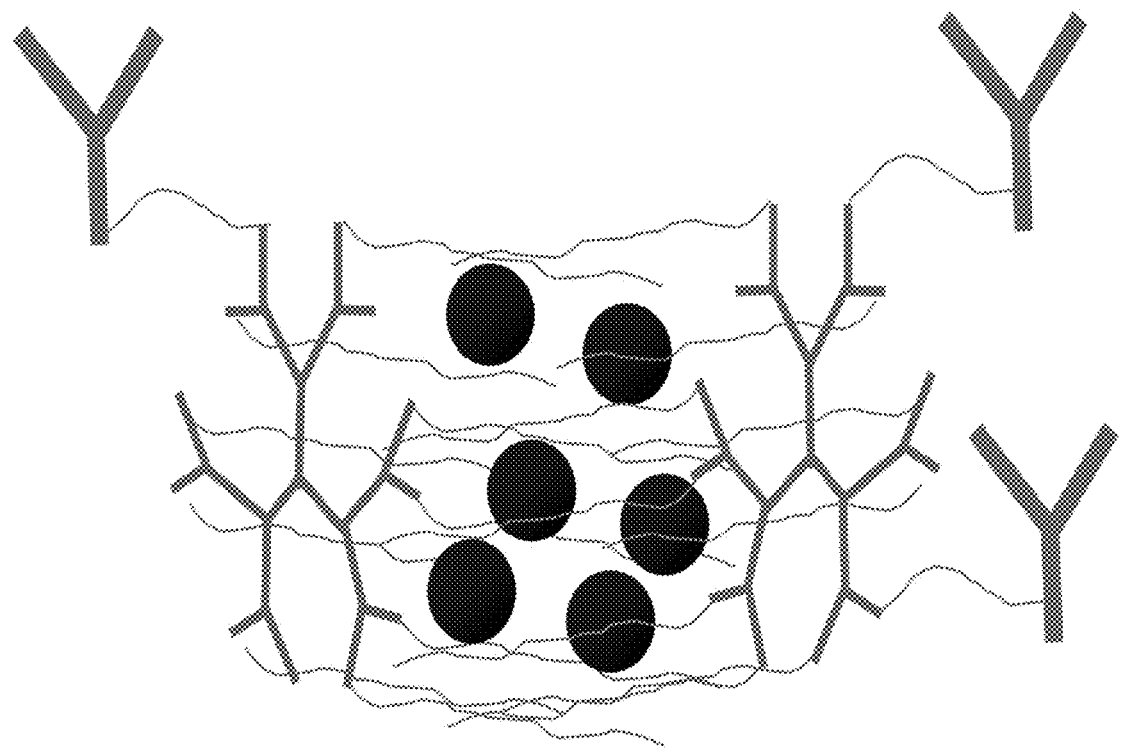
FIGS. 10A and 10B illustrate various drug-containing nanoparticles also carrying at least one targeting group or moiety, such as, an antibody, depicted herein and in other figures as a, "Y.
Figure 10B:
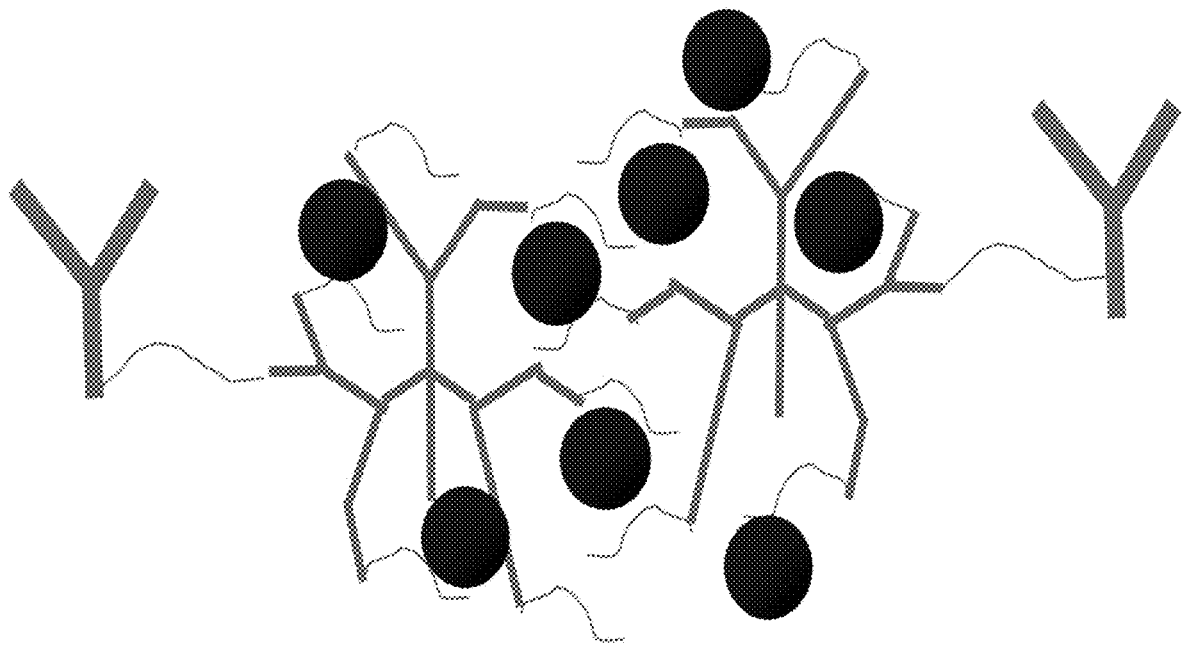

While the introduction of a primary amine group to a hydrophobically modified branched poly(2-oxazoline) homopolymer enhances drug solubility and produces PAA induced aggregates, the primary amine group also allows the attachment of various targeting groups, such as, an antibody, antigen binding portion thereof, an antigen, or a member of a binding pair to the hydrophobically modified branched poly(2-oxazoline) polymer (FIG. 10). Such aggregates or nanoparticles containing such targeting groups and modifications thereto can provide a targeting ability on the aggregate with PAA and enables PAA to be released preferentially or solely at the desired treatment location.

As taught herein, the MBP's, such as, a hydrophobically modified homopolymers, including both SBP's and ABP's, can be used to generate a surface-modified branched polymer for solubilizing water insoluble or poorly water soluble PAA's, or for forming PAA induced nanoparticles with water insoluble or poorly water soluble PAA's, such as, paclitaxel, camptothecin, doxorubin, dolargin, loperamide, tubocurarine, ibuprofen, diazepam, naproxen, carbamazepine, griseofulvin, nifedipine, phytosterol, omeprazol, domperidone, zidovudine, amphotericin B and the like, as well as drugs described herein, and known to be or are modified to be poorly soluble in water or insoluble in water. In such a reaction, the hydrophilic or amphiphilic core can be poly(2-oxazoline), poly(2-substituted oxazolines), including poly(2-methyloxazoline, poly(2-ethyloxazoline), poly(2-propyloxazoline) and poly(2-butyloxazoline) etc., PEG, PEO, polyphosphonate and the like. The hydrophobic shell can comprise aliphatic hydrocarbons (such as, from $C_1$ to about $C_{22}$), aromatic hydrocarbons, polyethylene polymers, polystyrene polymers, perfluoropolymers, polydimethylsiloxanes, polyacrylates, polymethylmethacrylates and the like. On the other hand, asymmetrically branched PLL, PEI or PEOX homopolymers also can be modified with hydrophobic surface groups listed above to enhance the solubility of water insoluble or poorly water soluble PAA's.

The branching density (e.g., from low generation, such as, star and comb homopolymers, to high generation of dendrimers and dendrigrafts), as well as the amount of hydrophobic surface group coverage (e.g., from 0% to 100% coverage) of the branched homopolymers can affect significantly homopolymer solubility, which in turn, also affects the ability to dissolve or to adsorb hydrophobic PAA's. For example, the increase in branching density and the amount of hydrophobic group coverage will make the homopolymer more compatible with hydrophobic PAA's.

In some cases, the ABP's and SBP's with from about 1 to about 30% or more surface hydrophobic component by weight are effective at solubilizing or dispersing poorly water soluble or water insoluble PAA's, such as, paclitaxel. In addition, the branched homopolymers utilized, for example, a PDX, a PEOX, a PMOX, PEO/PEG, polyacrylamides, polyphosphates, polyvinylpyrrolidones and polyvinyl alcohols are soluble in both water and in various organic solvents, thereby facilitating forming various PAA containing nanoparticles or aggregates. The good water solubility along with good hydrophobic drug miscibility in an aqueous solution, with or without other organic solvents, makes such homopolymers useful for enhancing the solubility of poorly water soluble PAA's. For example, the homopolymers of interest simplify manufacturing processes and decrease production cost by reducing formulation steps, processing time, as well as the need to use complex and expensive equipment currently used in the pharmaceutical industry. If additional branching densities are needed, the SBP's or ABP's first can be modified with additional groups as described herein, and then, for example, attached with additional hydrophobic functional groups for enhancing PAA solubility.

Figure 13:
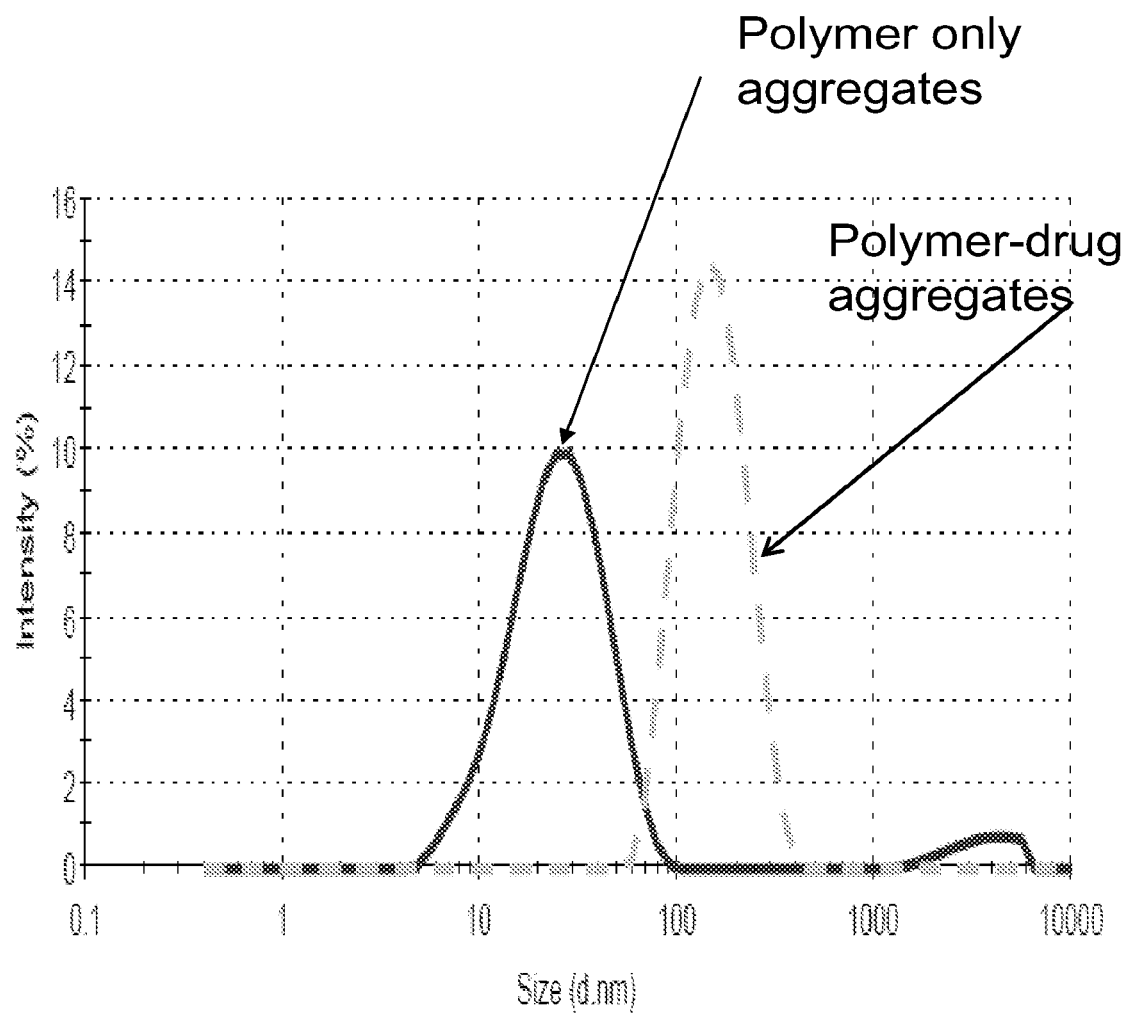
FIG. 13 shows the size comparison of polymer-only and polymer-drug aggregates with the polymer concentration at 25 mg/mL and the drug concentration at 5 mg/mL in saline. The polymer is a hydrophobically-modified, randomly-branched PEOX and the drug is paclitaxel.
Figure 14:
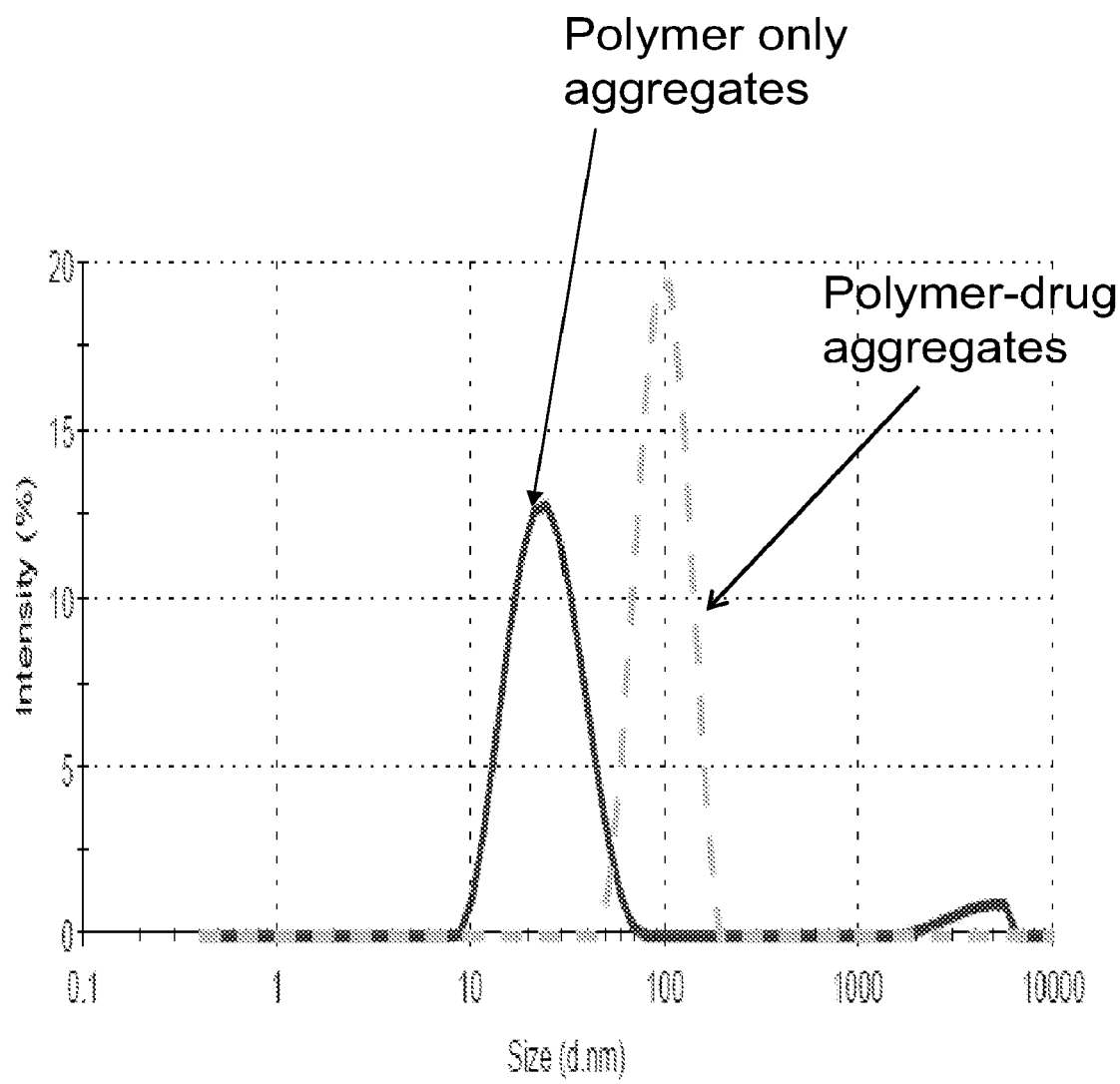
FIG. 14 shows the size comparison of polymer-only and polymer-drug aggregates with the polymer concentration at 2.5 mg/mL and the drug concentration at 0.5 mg/mL in saline. The polymer is a hydrophobically-modified, randomly-branched PEOX and the drug is paclitaxel.
Figure 15:
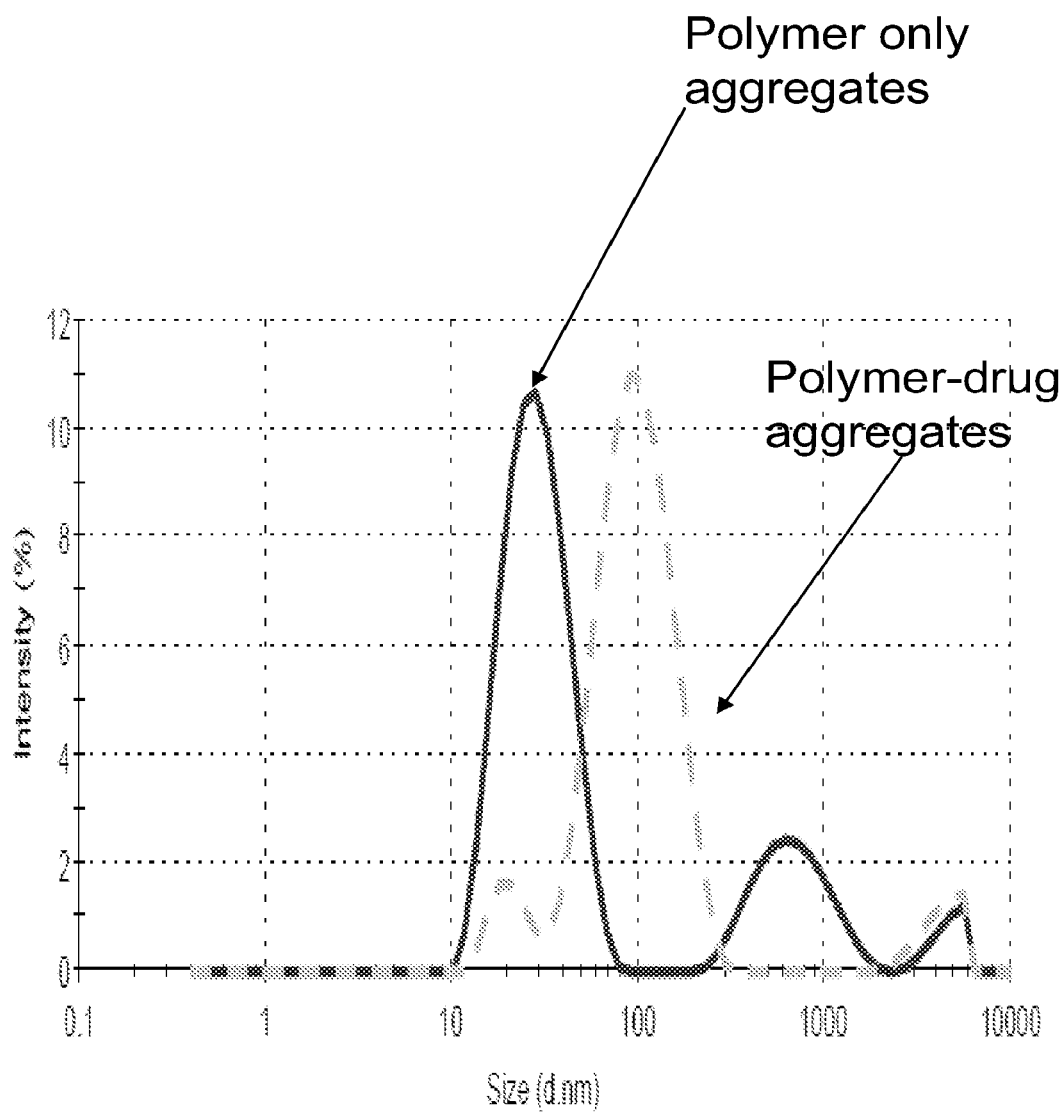
FIG. 15 shows the size comparison of polymer-only and polymer-drug aggregates with the polymer concentration at 250 µg/mL and the drug concentration at 50 µg/mL in saline. The polymer is a hydrophobically-modified, randomly-branched PEOX and the drug is paclitaxel.
Figure 16:
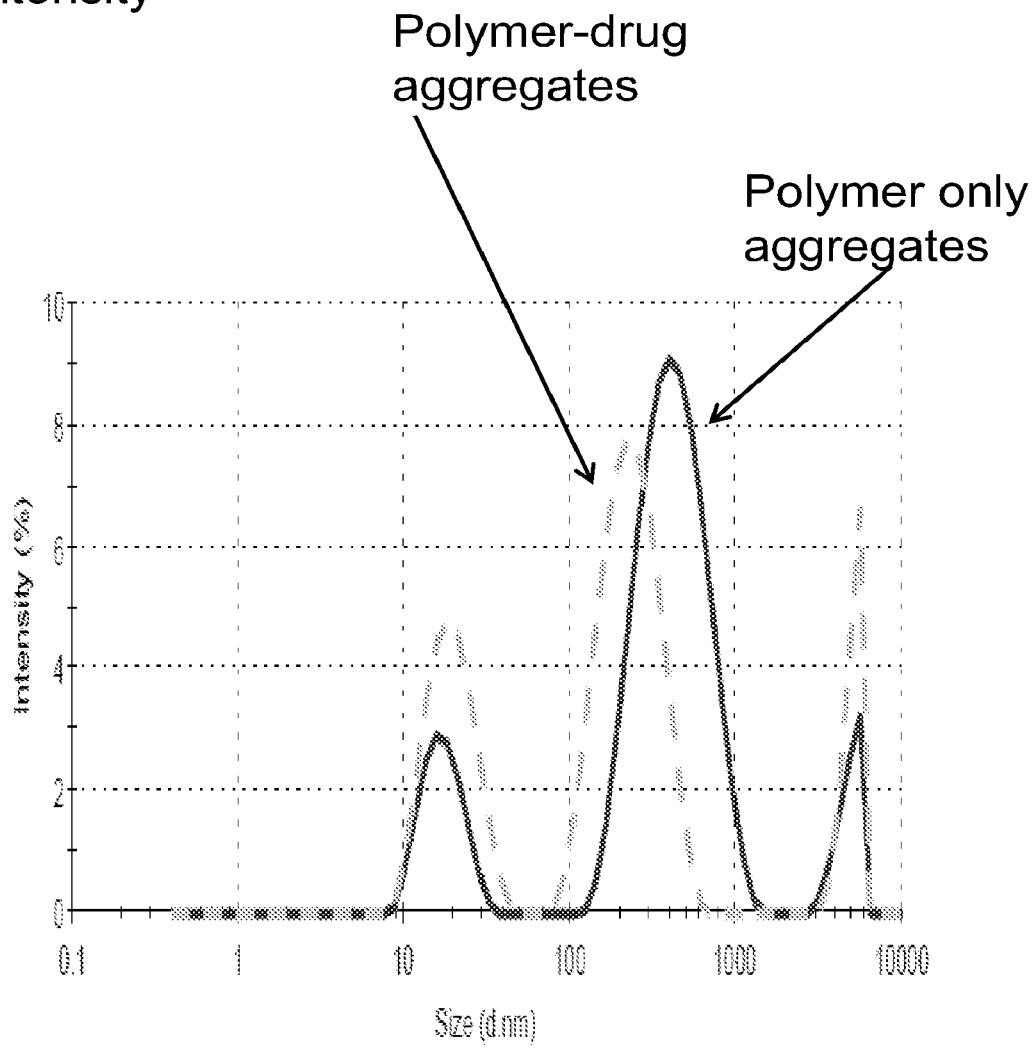
FIG. 16 shows the size comparison of polymer-only and polymer-drug aggregates with the polymer concentration at 25 µg/mL and the drug concentration at 5 µg/mL in saline. The polymer is a hydrophobically-modified, randomly-branched PEOX and the drug is paclitaxel.

On mixing hydrophobically modified SBP's or ABP's with a water insoluble or poorly water soluble PAA, a distinct physical aggregate is formed of size distinct from aggregates formed only of polymer (FIGS. 13-15). When the homopolymer and PAA concentrations decrease, the size and distribution of the polymer PAA aggregates become much more similar to that of polymer only aggregates suggesting PAA is released from the induced aggregates or nanoparticles. The broad size distribution of polymer only aggregates is similar to that observed for other structures composed of lipid, whether or not associated with a PAA. On the other hand, the PAA induced aggregates of interest are of a particular size of narrower distribution, that is, unique aggregates of certain size are produced. As PAA concentration in the aggregate decreases, homopolymer concentration in the aggregate decreases, aggregate concentration decreases or any combination thereof, the aggregates of interest release PAA, as evidenced by a reduction of aggregate size and/or a broader distribution of aggregate size. The broader distribution may result from a mixture of homopolymer only aggregates and polymer PAA aggregates of varying size due to PAA release, until the only aggregates observed are those which have the characteristics of those which are homopolymer only. In other words, the PAA is released gradually after introduced into a host, such as, in the circulatory system. That mechanism is important for various drug delivery applications including, intravenous (IV), oral, transdermal, ocular, intramuscular and the like modes of administration, and where a delayed release or sustained release profile may be desirable.

The PAA induced aggregates also can be linked with a targeting moiety or group including, but not limited to, an antibody (or antigen-binding portion thereof), antigen, cognate carbohydrates (e.g., sialic acid), a cell surface receptor ligand, a moiety that binds a cell surface receptor, a moiety that binds a cell surface saccharide, an extracellular matrix ligand, a cytosolic receptor ligand, a growth factor, a cytokine, an incretin, a hormone, a lectin, a lectin target, such as, a galactose, a galactose derivative, an N-acetylgalactosamine, a mannose, a mannose derivative and the like, a vitamin, such as, a folate, a biotin and the like, an avidin, a streptavidin, a neutravidin, a DNA, an RNA etc. to form a conjugate so that the targeting group(s) are incorporated with nanocomposite particle of interest (FIG. 10).

Figure 11A:
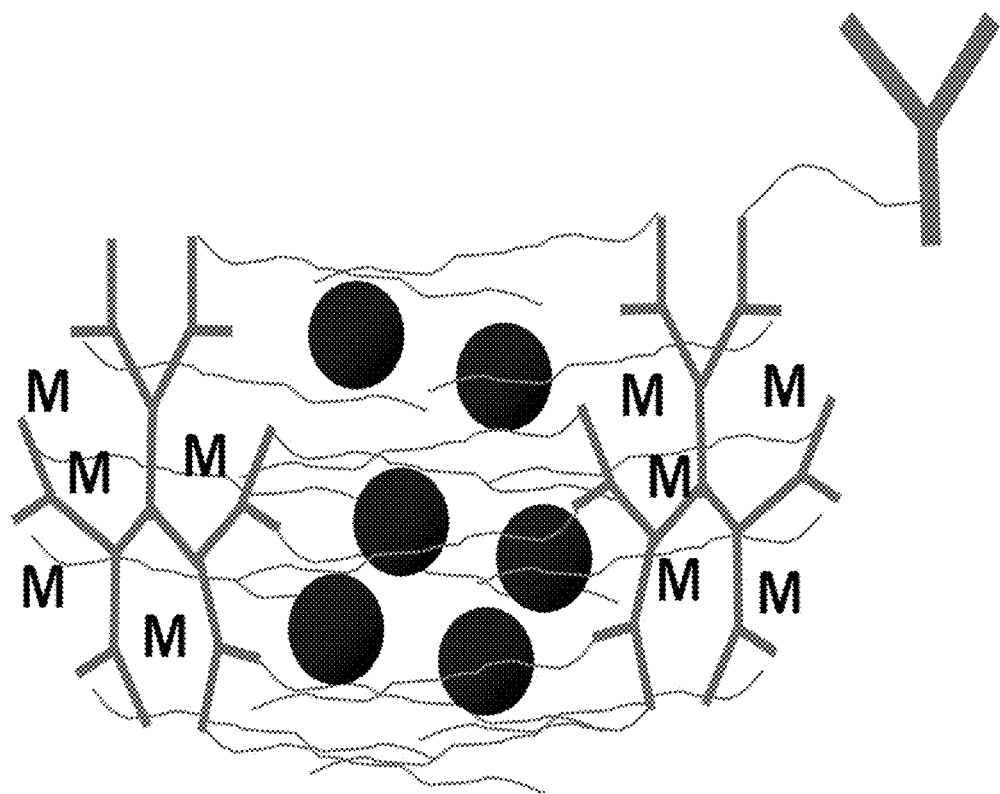
FIGS. 11A and 11B illustrate drug-containing nanoparticles carrying both magnetic imaging contrast agents and a targeting moiety or group, such as an antibody. In this and other Figures, M denotes an imaging material, such as, a magnetic resonance imaging contrast agent.
Figure 11B:
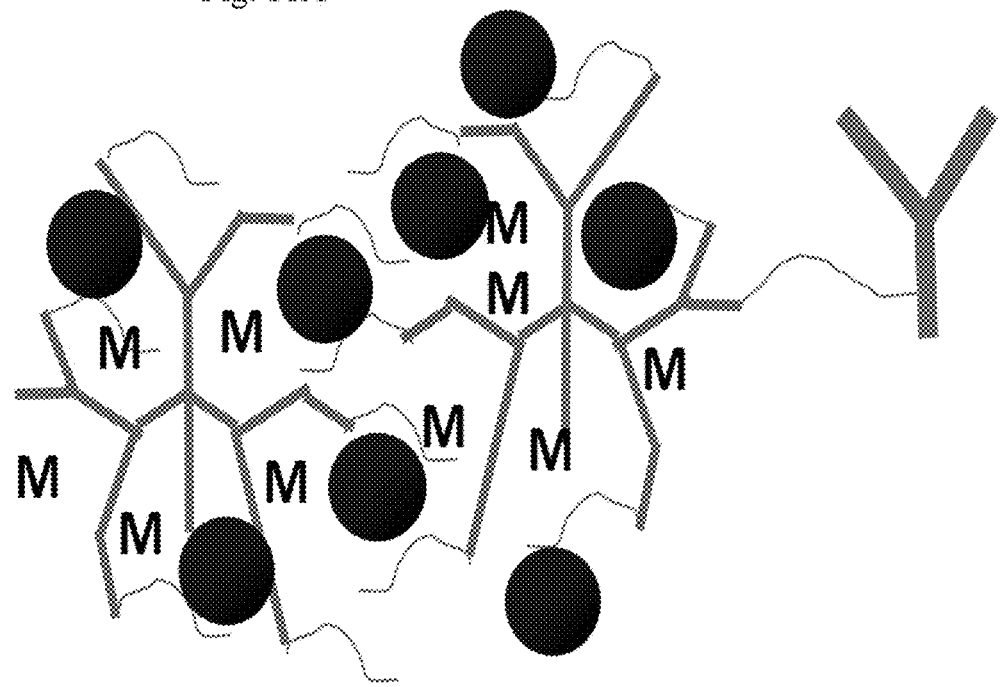
Figure 12A:
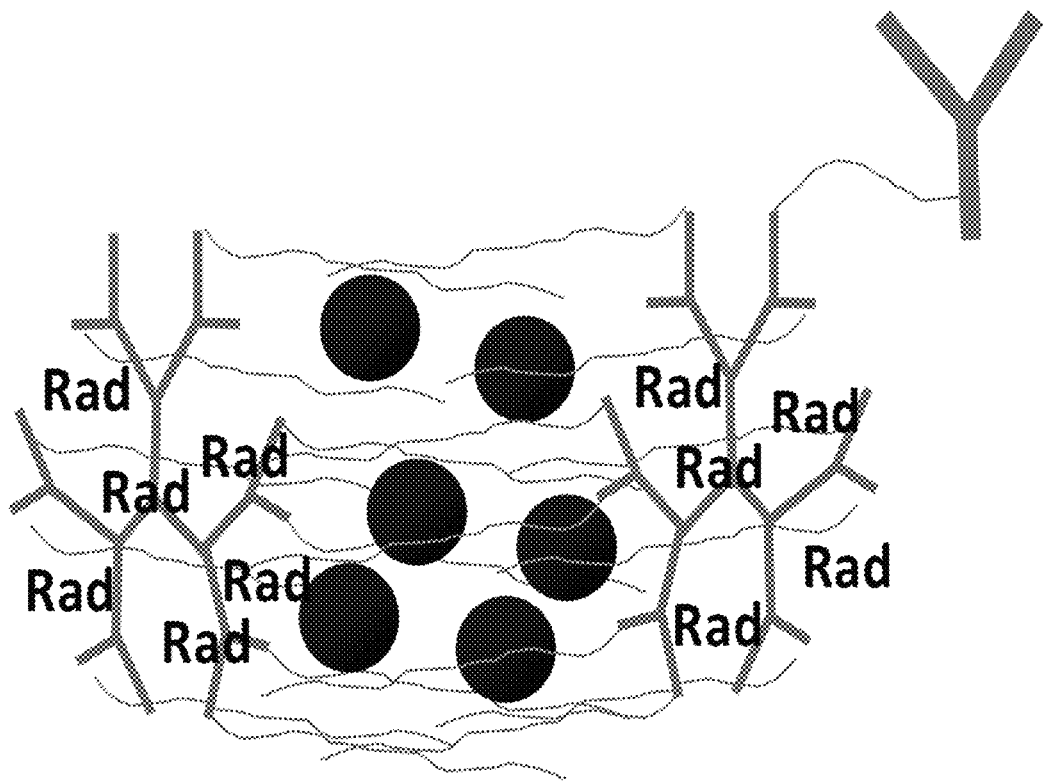
FIGS. 12A and 12B illustrate drug-containing nanoparticles carrying both radioactive (Rad) agents and a targeting moiety or group, such as, an antibody.
Figure 12B:
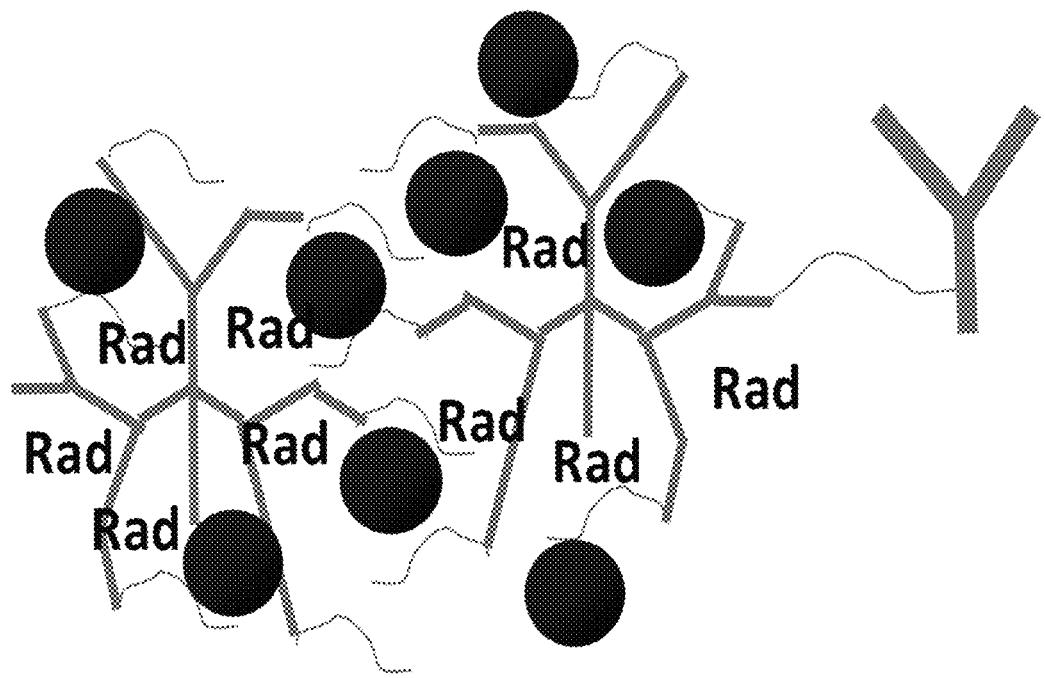

In addition, a diagnostic agent, such as, an imaging agent, a radionuclide or any of a variety of contrasting agents also can be carried by said aggregates of interest. Thus, a combination of chemotherapy, radiotherapy and/or targeted therapy with real time diagnostic/monitoring capabilities can be achieved (FIGS. 11 and 12). In some embodiments, the diagnostic agent is poorly soluble or water insoluble, thereby negating the need, for example, of a PAA of interest to induce aggregation.

Thus, a diagnostic agent can be a metal containing material or a paramagnetic material, e.g., magnetic resonance imaging materials, which can be deposited on the surface or entrapped within a nanocomposite of interest so that the nanoparticle can be used as both a diagnostic and a therapeutic agent. In yet another aspect of the disclosure, the imaging material containing nanoparticles further can comprise a targeting moiety/group, which allows such nanoparticle to target specific locations that need therapeutic treatment, for example, a tumor site.

Thus, a molecule with the ability to bind another molecule, such as a biological polymer, such as a polypeptide, or a polysaccharide, an enzyme, a receptor and the like, which can bind a vitamin, a lectin, a metal and so on, can be used in a composite of interest. Metals and metal ions that can be carried by a polymer of interest may include, but are not limited to, transition metals, such as Sc, Y, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd Hg, Ga, In or Tl, alkali metals, alkaline earth metals, Lanthanide series elements, such as Ce, Pr, Nd, Pm, Sm, Eu, Gd, Tb, Dy, Ho, Er, Tm, Yb and Lu, Actinide series elements, such as Th, Pa, U, Np, Pu, Am, Cm, Bk, Cf, Es, Fm, Md, No and Lr, and the like.

Such can be carried by, for example, one or more chelating groups, including, but not limited to, ethylenediaminetetraacetic acid (EDTA), diethylenetriaminepentaacetic acid (DTPA), diethylenetriaminepentaacetic acid (DTPA), 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (DOXA), 1,4,7-triazacyclononanetriacetic acid (NOTA), 1,4,8,11-tetraazacyclotetradecanetetraacetic acid (TETA), DOTA-N(2-aminoethyl)amide and DOTA-N-(2-aminophenethyl)amide.

For such diagnostic purposes, a conjugate of interest comprises a reporter molecule that can be detected by an external device, such as, a gamma camera. Thus, a conjugate can be configured to comprise, for example, a radioisotope that will emit detectable radiation. The conjugate is placed into a format suitable for consumption or placement in a body, employing reagents suitable therefor as known in the art. The conjugate composition is administered as known in the art, such as, orally, rectally, intravenously and so on.

In another aspect of the disclosure, the nanoparticle can carry different types of PAA's so that a combination or cocktail therapy can be achieved. Such PAA's may include, but are not limited to, various small molecule drugs, inorganic drugs and biological molecule based drugs, such as, a peptide, a protein, an antibody, an enzyme, a vaccine and the like. The second or more PAA's need not be poorly soluble or water insoluble as the second or more PAA's can be situated within voids in the aggregate and need not be located at the surface. Hence, any of the PAA's noted herein or known in the art can comprise the second or more PAA's.

Drug Formulation and Nanoparticle Preparation

PAA and modified homopolymer can be suspended individually in suitable buffers and/or solvents, such as, a buffer, acetone, ethanol and the like, at suitable concentrations, such as those which are established for in vivo use, generally in milligram or nanogram quantities. Then, the two solutions are mixed at a suitable temperature, such as, room temperature or at another temperature known to be acceptable for maintaining integrity of the PAA and homopolymer, for a suitable period of time, such as, one hour, two hours and so on. Other incubation times can vary from minutes to hours as the aggregates of interest are stable once formed. The aggregates can be concentrated or collected practicing methods known in the art, for example, by filtration, centrifugation, evaporation, lyophilization, dialysis and the like. The aggregates can be desiccated for extended shelf life.

For example, paclitaxel was dissolved in ethanol in various amounts of up to 40 mg/mL. A hydrocarbon ($CH_3(CH_2)_{17}$) modified randomly branched PEOX was prepared as taught herein and dissolved at varying concentrations of up 100 mg/mL in saline.

The two solutions then were mixed in various volumes to result in final homopolymer to paclitaxel molar ratios in the mixtures ranging from 3:1 to 10:1. The mixtures subsequently were frozen at −80° C. for 3 hours then lyophilized for 20 to 48 hours depending on volume to yield a dry powder.

The size of the aggregates or nanoparticles, as measured by light scattering, can range from about 120 nm (e.g., at 3 mg paclitaxel per mL) to about 165 nm (e.g., at 5 mg paclitaxel per mL) in diameter depending on the concentration of drug and concentration of homopolymer.

Alternatively, PAA and homopolymer can be dissolved in a common solvent, which generally is not necessarily hydrophilic but is miscible with water, and then added to an aqueous solution. Hence, paclitaxel and PEOX can be dissolved in acetone and then dropwise added to water under agitation, such as, while stirred or sonicated, followed by dialysis with a 1000 MW cutoff membrane. The final product then can be lyophilized.

A conjugate of interest can be incorporated into pharmaceutical compositions suitable for administration, for example, for diagnostic imaging, for lifestyle management or to attain a therapeutic milestone. Such compositions typically comprise an aggregate of interest and a pharmaceutically acceptable carrier, excipient or diluent, which is intended to include any and all solvents, dispersion media, coatings, antibacterial and antifungal agents, isotonic and absorption delaying agents and the like, that is, those ingredients of a pharmaceutically acceptable composition aside from the PAA's that are included therein for particular purposes, such as, bulking, preservation, delayed release, binding and so on, as known in the art, compatible with pharmaceutical administration. The use of such media and agents for pharmaceutically active substances is well known in the art. Except insofar as any conventional media or agents are incompatible with the active compound, use thereof in the compositions is contemplated. Supplementary active compounds also can be incorporated into the composition.

A pharmaceutical composition of the disclosure for use as disclosed herein is formulated to be compatible with the intended route of administration. Examples of routes of administration include parenteral, e.g., intravenous, intradermal, subcutaneous, oral (e.g., inhalation), transdermal (topical), transmucosal and rectal administration. Solutions or suspensions used for parenteral, intradermal or subcutaneous application can include a sterile diluent, such as, water for injection, saline, oils, polyethylene glycols, glycerine, propylene glycol or other synthetic solvents; antibacterial agents, such as, benzyl alcohol or methyl parabens; antioxidants, such as, ascorbic acid or sodium bisulfite; chelating agents, such as, EDTA; buffers, such as, acetates, citrates or phosphates; and agents for the adjustment of tonicity, such as, sodium chloride or dextrose. pH can be adjusted with acids or bases, such as HCl or NaOH. The parenteral preparation can be enclosed in ampoules, disposable syringes or multiple dose vials made of glass or plastic as an article of manufacture. Generally, an in vivo diagnostic agent will be administered orally, rectally, intravenously, intraperitoneally and so on.

Pharmaceutical compositions suitable for injectable use include sterile aqueous solutions or dispersions and sterile powders for the extemporaneous preparation of sterile injectable solutions or dispersions. For intravenous administration, suitable carriers include physiological saline, bacteriostatic water or phosphate-buffered saline (PBS). The composition generally is sterile and is fluid to the extent that easy syringability exists. The composition must be stable under the conditions of manufacture and storage and must be preserved against the contaminating action of microorganisms, such as, bacteria and fungi. The carrier can be a solvent or dispersion medium containing, for example, water, ethanol, polyol (for example, glycerol, propylene glycol, liquid polyethylene glycol and the like) and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. Isotonic agents, for example, sugars, polyalcohols, such as, mannitol, sorbitol or sodium chloride can be included in the composition. Prolonged absorption of the injectable compositions can be brought about by including in the composition an agent that delays absorption, for example, aluminum monostearate or gelatin.

Sterile injectable solutions can be prepared by incorporating the active compound in the required amount of an appropriate solvent with one or a combination of ingredients enumerated above, as required, followed by filtered sterilization. Generally, dispersions are prepared by incorporating the active compound in a sterile vehicle that contains a basic dispersion medium and the required other ingredients, for example, from those enumerated above, and as known in the art. In the case of sterile powders for the preparation of sterile injectable solutions, the preparation can be prepared by, for example, lyophilization, vacuum drying or freeze drying, that yields a powder of the active ingredient plus any additional desired ingredient from a previously sterile-filtered solution thereof. The preparation of interest can be stored and reconstituted with a suitable liquid for use.

Oral compositions generally include an inert diluent, flavorant, odorant or an edible carrier. The composition can be enclosed in gelatin capsules or compressed into tablets. For the purpose of oral therapeutic administration, the active compound can be incorporated with excipients and used in the form of tablets, troches or capsules. Oral compositions also can be prepared using a fluid carrier to yield a syrup or liquid formulation, or for use as a mouthwash, wherein the compound in the fluid carrier is applied orally and swished and expectorated or swallowed.

Pharmaceutically compatible binding agents and/or adjuvant materials can be included as part of the composition. Tablets, pills, capsules, troches and the like can contain a binder, such as, microcrystalline cellulose, gum tragacanth or gelatin; an excipient, such as, starch or lactose, a disintegrating agent, such as, alginic acid, Primogel or corn starch; a lubricant, such as, magnesium stearate or Sterotes; a glidant, such as, colloidal silicon dioxide; a sweetening agent, such as, sucrose or saccharin; or a flavoring agent, such as, peppermint, methyl salicylate or orange flavoring.

For administration by inhalation, the compound is delivered in the form of, for example, a wet or dry aerosol spray from a pressurized container or dispenser that contains a suitable propellant, e.g., a gas, such as, carbon dioxide or a nebulizer, or a mist.

Systemic administration also can be by transmucosal or transdermal means. For transmucosal or transdermal administration, penetrants appropriate to the barrier to be permeated are used in the formulation. Such penetrants generally are known in the art and include, for example, for transmucosal administration, detergents, bile salts and fusidic acid derivatives. Transmucosal administration can be accomplished through the use of nasal sprays or suppositories. For transdermal administration, the active compounds are formulated into ointments, salves, gels or creams as generally known in the art. A suitable carrier includes dimethylsulfoxide.

The compound also can be prepared in the form of suppositories (e.g., with conventional suppository bases, such as, cocoa butter and other glycerides) or retention enemas for rectal delivery.

In one embodiment, the active compound is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid.

Methods for preparation of such formulations will be apparent to those skilled in the art. The materials also can be obtained commercially, for example, from Alza Corporation and Nova Pharmaceuticals, Inc.

The instant aggregates can be used in topical forms, such as, creams, ointments, lotions, unguents, other cosmetics and the like. PAA's and other bioactive or inert compounds can be carried, and include emollients, bleaching agents, antiperspirants, pharmaceuticals, moisturizers, scents, colorants, pigments, dyes, antioxidants, oils, fatty acids, lipids, inorganic salts, organic molecules, opacifiers, vitamins, pharmaceuticals, keratolytic agents, UV blocking agents, tanning accelerators, depigmenting agents, deodorants, perfumes, insect repellants and the like.

It can be advantageous to formulate oral or parenteral compositions in dosage unit form for ease of administration and uniformity of dosage. Dosage unit form as used herein refers to physically discrete units suited as unitary dosages for a subject to be treated; each unit containing a predetermined quantity of active compound calculated to produce a desired therapeutic endpoint.

The dosages, for example, preferred route of administration and amounts are obtainable based on empirical data obtained from preclinical and clinical studies, practicing methods known in the art. The dosage and delivery form can be dictated by and can be dependent on the characteristics of the PAA, the polymer, the particular therapeutic effect to be achieved, the characteristics and condition of the recipient and so on. For repeated administrations over several days or longer, depending on the condition, the treatment can be sustained until a desired endpoint is attained. An exemplary dosing regimen is disclosed in WO 94/04188.

The progress of the therapy can be monitored by conventional techniques and assays, as well as patient input.

The pharmaceutical compositions can be included in a container, pack or dispenser together with instructions for administration.

Another method of administration comprises the addition of a compound of interest into or with a food or drink, as a food supplement or additive, or as a dosage form taken on a prophylactic basis, similar to a vitamin. The aggregate of interest can be encapsulated into forms that will survive passage through the gastric environment. Such forms are commonly known, for example, enteric coated formulations. Alternatively, the aggregate of interest can be modified to enhance half life, such as, chemical modification or combination with agents known to result in delayed, sustained or controlled release, as known in the art.

The instant disclosure now will be exemplified in the following non-limiting examples.

EXAMPLES

Materials

Symmetrically branched PPI dendrimers were purchased from Sigma-Aldrich. Symmetrically branched PEI dendrimers and dendrigrafts were prepared according to procedures provided in U.S. Pat. Nos. 4,631,337, 5,773,527, 5,631,329 and 5,919,442. All of the antibodies were purchased from Sigma-Aldrich, Biodesign or Fitzgerald. Different generation PAMAM dendrimers were purchased from Dendritech, Inc.

Synthesis of Modified Symmetrically Branched PPIs with Amino Functional Groups (m-SB-PPI-NH$_2$-1.0)

The following reagents including symmetrically branched PPI (SB-PPI-4, 8, 16, 32, 64, MW 316, 773, 1,687, 3,514 and 7,168), methyl acrylate (MA, FW=86.09), ethylenediamine (EDA, FW=60.10) and methanol were utilized.

To a round bottom flask were added 1.0 g PPI-64 dendrimer (MW 7168) and 20 ml methanol (solution A). To a separate round bottom flask were added 2.4 g methylacrylate (MA) and 10 ml methanol (solution B). Solution A was then slowly dropped into solution B while stirring at room temperature. The resulting solution was allowed to react at 40° C. for 2 hours. On completion of the reaction, the solvent and unreacted MA monomer were removed by rotary evaporation and the product, 2.5 g of MA functionalized PPI, then was redissolved in 20 ml of methanol.

To a round bottom flask were added 160 g EDA and 50 ml of methanol, followed by a slow addition of MA functionalized PPI at 0° C. The solution then was allowed to react at 4° C. for 48 hours. The solvent and the excess EDA were removed by rotary evaporation. The crude product then was precipitated from an ethyl ether solution and further purified by dialysis to give about 2.8 g of primary amine-functionalized symmetrically branched PPI (m-SB-PPI-NH$_2$-1.0) with a molecular weight of about 21,760. The product was characterized by $^1$H and $^{13}$C nuclear magnetic resonance (NMR) and size exclusion chromatography (SEC).

Other MA or primary amine-modified symmetrically branched PPI dendrimers and symmetrically branched PEI dendrigrafts with various molecular weights were prepared in a similar manner.

Synthesis of Modified Symmetrically Branched PPIs with Mixed Hydroxyl and Amino Functional Groups (mix-m-SB-PPI-64-NH$_2$/OH-2)

Amino functionalized symmetrically branched PPI (m-SB-PPI-64-NH$_2$-1.0), MA, EDA, monoethanolamine (MEA, FW=61.08) and methanol were utilized.

To a round bottom flask were added 1.0 g amino-modified PPI or m-SB-PPI-NH$_2$-1.0 produced from the previous procedure and 20 ml of methanol (solution A). To a separate round bottom flask were added 2.4 g of MA and 10 ml methanol (solution B). Solution A was then slowly dripped into solution B while stirring at room temperature. The resulting solution was allowed to react at 40° C. for 2 hours. On completion of the reaction, the solvent and unreacted monomer MA were removed by rotary evaporation and the product, 2.5 g of MA functionalized m-SB-PPI-64-MA-1.5, then was redissolved in 20 ml of methanol.

To a round bottom flask were added 32 g EDA, 130 g MEA and 100 ml methanol (the mole ratio of EDA:MEA was 20:80), followed by slow addition of m-SB-PPI-64-MA-1.5 at 0° C. The solution then was allowed to react at 4° C. for 48 hours. The solvent and the excess EDA were removed by rotary evaporation. The crude product then was precipitated from an ethyl ether solution and further purified by dialysis to give about 2.8 g of mixed hydroxyl and amino functionalized (mixed surface) SBP (mix-m-SB-PPI-64-NH$_2$/OH-2.0, with an average of 20% NH$_2$ and 80% OH surface groups and a molecular weight of about 21,862).

Other modified random AB-PEI and regular AB PLL molecules with varying ratios of hydroxyl and amino groups, as well as different molecular weights, were prepared in a similar manner.

Random asymmetrically branched PEI's were purchased from Aldrich and Polysciences. Regular ABP's were prepared according to procedures provided in U.S. Pat. No. 4,289,872. All of the antibodies were purchased from Sigma-Aldrich, Biodesign or Fitzgerald.

Synthesis of Modified Random Asymmetrically Branched PEIs with Amino Functional Groups (m-Ran-AB-PEI-NH$_2$-1.0)

Random asymmetrically branched PEI (ran-AB-PEI, MW 2,000, 25,000 and 75,000), MA, EDA and methanol were utilized.

To a round bottom flask were added 1.0 g PEI (MW 2,000) and 20 ml methanol (solution A). To a separate round bottom flask were added 3.0 g MA and 10 ml methanol (solution B). Solution A was then slowly dripped into solution B while stirring at room temperature. The resulting solution was allowed to react at 40° C. for 2 hours. On completion of the reaction, the solvent and unreacted MA were removed by rotary evaporation and the product, MA functionalized PEI, then was redissolved in 20 ml of methanol.

To a round bottom flask were added 80 g EDA and 50 ml of methanol, followed by a slow addition of MA-functionalized PEI at 0° C. (1 g MA dissolved in 20 ml methanol). The solution then was allowed to react at 4° C. for 48 hours. The solvent and excess EDA were removed by rotary evaporation. The crude product then was precipitated from an ethyl ether solution and further purified by dialysis to give about 3.0 g of primary amine-functionalized random asymmetrically branched PEI (m-ran-AB-PEI-NH$_2$-1.0) with a molecular weight of about 7,300. The product was characterized by $^1$H and $^{13}$C NMR and SEC.

Other MA or primary amine modified random asymmetrically branched PEI and regular asymmetrically branched PLL polymers with various molecular weights were prepared in a similar manner.

Modification of Branched Polymers with Hydrocarbon Chains

The modification of a randomly branched PEI with 10% hydrocarbon chains is used as an example. One gram of branched PEI (FW=25000) was dissolved in 10 mL methanol. To the solution were added 0.23 g of 1,2-epoxyhexane (FW=100.16) and the mixture was heated at 40° C. for 2 hours. The solvent then was rotary evaporated and the residue redissolved in water. After dialysis (3,500 cutoff), the modified PEI was generated. Other MBP's, such as, PAMAM, PEI and PPI dendrimers and dendrigrafts, and asymmetric PLL with various percentages and lengths (e.g., $C_4$, $C_{12}$, $C_{18}$ and $C_{22}$) of hydrocarbon chains were prepared in a similar manner.

Synthesis of Modified Random Asymmetrically Branched PEIs with Mixed Hydroxyl and Amino Functional Groups (m-ran-AB-PEI-NH$_2$/OH-2)

Amino functionalized random asymmetrically branched PEI (m-ran-AB-PEI-NH$_2$-1.0), MA, EDA, monoethanolamine (MEA, FW=61.08) and methanol were utilized.

To a round bottom flask were added 1.0 g amino-modified PEI or m-ran-AB-PEI-NH$_2$-1.0 produced from the previous procedure and 20 ml of methanol (solution A). To a separate round bottom flask were added 3.0 g of MA and 10 ml methanol (solution B). Solution A then was slowly dripped into solution B while stirring at room temperature. The resulting solution was allowed to react at 40° C. for 2 hours. On completion of the reaction, the solvent and unreacted MA were removed by rotary evaporation and the product, MA functionalized m-ran-AB-PEI-MA-1.5, then was redissolved in 20 ml of methanol.

To a round bottom flask were added 60 g EDA, 244 g MEA and 100 ml methanol (the mole ratio of EDA:MEA was 20:80), followed by slow addition of m-ran-AB-PEI-MA-1.5 at 0° C. (1 g MA dissolved in 20 ml of methanol). The solution then was allowed to react at 4° C. for 48 hours. The solvent and excess EDA were removed by rotary evaporation. The crude product then was precipitated from an ethyl ether solution and further purified by dialysis to give about 2.4 g of mixed hydroxyl and amino functionalized random ABP (m-ran-AB-PEI-NH$_2$/OH-2.0, with an average of 20% NH$_2$ and 80% OH surface groups and the molecular weight was about 18,000).

Other modified random AB-PEI and regular AB polylysine polymers with various ratios of hydroxyl and amino groups, as well as different molecular weights were prepared in a similar manner.

Synthesis of Alkyl-Modified Random Asymmetrically Branched Poly(2-ethyloxazoline) (PEOX) with Primary Amine Chain End Group The synthesis of CH$_3$—(CH$_2$)$_{11}$-PEOX-ABP100 (ABP100 is an arbitrary name to denote the ratio of monomer to initiator in the initial reaction) is provided as a general procedure for the preparation of core shell structures. A mixture of CH$_3$(CH$_2$)$_{11}$—Br (2.52 g) in 500 ml of toluene was azeotroped to remove water with a distillation head under N$_2$ for about 15 min. 2-Ethyloxazoline (100 g) was added dropwise through an addition funnel and the mixture was allowed to reflux between 24 and 48 hours. On completion of the polymerization, 12.12 g of EDA were added to the reactive polymer solution (A) to introduce the amine function group. The molar ratio of polyoxazoline chain end to EDA was 1 to 20.

N-tert-butyloxycarbonylpiperazine (N-Boc-piperazine) or water (e.g., with 1N Na$_2$CO$_3$) can be added to terminate the reaction. Morpholine or PEI also can be added to the reactive polymer solution (A) to terminate the reaction. The crude product was redissolved in methanol and then precipitated from a large excess of diethyl ether. The bottom layer was redissolved in methanol and dried by rotary evaporation and vacuum to give an asymmetrically random branched PEOX polymer or PEOX-PEI copolymer as a white solid (101 g). Other asymmetrically randomly branched polymers, such as, C$_6$-PEOX ABP20, 50, 100, 200, 300, 500, C$_{18}$-PEOX ABP20, 50, 200, 300, 500, C$_{22}$-PEOX ABP20, 50, 100, 200, 300, 500, and polystyrene-PEOX etc., as well as, non-modified and modified poly(2-substituted oxazoline), such as, poly(2-methyloxazoline), were prepared in a similar manner. All the products were analyzed by SEC and NMR.

Preparation of Mixed Surface Modified Symmetrical Branched Polymer-IgG Conjugates The preparation of mixed surface (OH/NH$_2$ mix) modified symmetrically branched PPI-IgG conjugates (mix-m-SB-PPI-64-NH$_2$/OH-2-IgG conjugates) is provided as a general procedure for the preparation of polymer antibody and polymer streptavidin conjugates. Other conjugates, such as, m-SB-PPI-4-NH$_2$-1-IgG, m-SB-PPI-8-NH$_2$-1-IgG, m-SB-PPI-16-NH$_2$-1-IgG, m-SB-PPI-32-NH$_2$-1-IgG, m-SB-PPI-4-NH$_2$-2-IgG, m-SB-PPI-8-NH$_2$-2-IgG, m-SB-PPI-16-NH$_2$-2-IgG, m-SB-PPI-32-NH$_2$-2-IgG, m-SB-PPI-4-NH$_2$-3-IgG, m-SB-PPI-8-NH$_2$-3-IgG, m-SB-PPI-16-NH$_2$-3-IgG, m-SB-PPI-32-NH$_2$-3-IgG, mix-m-SB-PPI-4-NH$_2$/OH-1 (OH/NH$_2$ mix)-IgG, mix-m-SB-PPI-8-NH$_2$/OH-1 (OH/NH$_2$ mix)-IgG, mix-m-SB-PPI-16-NH$_2$/OH-1 (OH/NH$_2$ mix)-IgG, mix-m-SB-PPI-32-NH$_2$/OH-1 (OH/NH$_2$ mix)-IgG, mix-m-SB-PPI-4-NH$_2$/OH-2 (OH/NH$_2$ mix)-IgG, mix-m-SB-PPI-8-NH$_2$/OH-2 (OH/NH$_2$ mix)-IgG, mix-m-SB-PPI-16-NH$_2$/OH-2 (OH/NH$_2$ mix)-IgG, mix-m-SB-PPI-32-NH$_2$/OH-2 (OH/NH$_2$ mix)-IgG, mix-m-SB-PPI-4-NH$_2$/OH-3 (OH/NH$_2$ mix)-IgG, mix-m-SB-PPI-8-NH$_2$/OH-3 (OH/NH$_2$ mix)-IgG, mix-m-SB-PPI-16-NH$_2$/OH-3 (OH/NH$_2$ mix)-IgG, mix-m-SB-PPI-32-NH$_2$/OH-3 (OH/NH$_2$ mix)-IgG, as well as primary amine and mix OH/NH$_2$ modified combburst PEI dendrigrafts (Generation 0-5) also were obtained in a similar manner. The synthesis of other protein attached to a modified SBP of interest also was obtained in a similar manner. The biotinylated-IgG conjugates were synthesized as provided in Bioconjugate Techniques (G. Hermanson, Academic Press, 1996).

LC-SPDP-Mixed Surface m-SB-PPI-64-NH$_2$/OH-2

To the mixed surface randomly branched mix-m-SB-PPI-64-NH$_2$/OH-2 ($4 \times 10^{-7}$ mol) in 400 μl of phosphate buffer (20 mM phosphate and 0.1 M NaCl, pH 7.5) were added $4.0 \times 10^{-6}$ mol of sulfo-LC-SPDP (Pierce, IL) in 400 μL of water. The mixture was vortexed and incubated at 30° C. for 30 minutes. The LC-SPDP-mix-m-SB-PPI-64-NH$_2$/OH-2 was purified by gel filtration chromatography and equilibrated with buffer A (0.1 M phosphate, 0.1 M NaCl and 5 mM EDTA, pH 6.8). The product was concentrated further to yield 465 μL of solution with a concentration of approximately 0.77 nmol.

Thiolated Mix m-SB-PPI-64-NH$_2$/OH-2 from LC-SPDP Mix-m-SB-PPI-64-NH$_2$/OH-2

The LC-SPDP mix-m-SB-PPI-64-NH$_2$/OH-2 (50 nmol in 65 μl of buffer A) was mixed with 100 μL of dithiothreitol (DTT) (50 mM in buffer A) and was incubated at room temperature for 15 minutes. Excess DTT and byproducts were removed by gel filtration with buffer A. The product was concentrated in a 10 K Centricon Concentrator to yield 390 µL of the thiolated mix-m-SB-PPI-64-NH$_2$/OH-2 that was used for conjugation with activated antibody.

Maleimide R (MAL-R)-Activated Antibody

To the antibody in PBS (310 µL, 5.1 mg or 34 nmol) were added 20.4 µL of a MAL-R-NHS (N-hydroxysuccinimide) solution (10 mM in water). The mixture was vortexed and incubated at 30° C. for 15 minutes. The product was purified by gel filtration with buffer A. The maleimide-R-activated antibody was used for conjugation with the thiolated mix-m-SB-PPI-64-NH$_2$/OH-2.

Mix-m-SB-PPI-64-NH$_2$/OH-2-Antibody Conjugate

To the thiolated mix-m-SB-PPI-64-NH$_2$/OH-2 (310 µL or 35.7 nmol) was added the MAL-R-activated antibody (4.8 mL or 34 nmol). The reaction mixture was concentrated to approximately 800 µL and then allowed to incubate overnight at 4° C. and/or at room temperature for about 1 hr. On completion, the reaction was quenched with 100 µL of ethyl maleimide (50 mmolar solution) and the conjugate then was fractionated on a carboxymethyl cellulose column (5 mL) with a sodium chloride step gradient in 20 mM phosphate buffer at pH 6. The conjugate was eluted with a sodium chloride gradient and characterized by cationic exchange chromatography, UV spectroscopy and polyacrylamide gel electrophoresis.

Conjugation Via Reductive Coupling

Reduction of Antibody

To the antibody, 2.1 mg or 14 nmol in 160 µL of buffer B (containing 0.1 M sodium phosphate, 5 mM EDTA and 0.1 M NaCl, pH 6.0) were added 40 µL of DTT (50 mM in buffer B). The solution was allowed to stand at room temperature for 30 min. The product was purified by gel filtration in a Sephadex G-25 column equilibrated with buffer B. The reduced antibody was concentrated to 220 µL and was used for conjugation.

MAL-R-Mixed Surface Modified SBP

To the mixed surface modified SBP in 400 µL (400×10$^{-9}$ mols) at pH 7.4 were added 400 µL of MAL-R-NHS (10 mM in water). That was mixed and incubated at 30° C. for 15 min. On termination, the product was purified on a Sephadex G-25 column equilibrated with buffer B. The MAL-R-mixed surface modified SBP was collected and stored in aliquots in the same buffer at −40° C.

Mixed Surface Modified SBP-Antibody Conjugate

To the reduced antibody (14 nmols in 220 µL) was added the MAL-R-mix-m-SB-PPI-64-NH$_2$/OH-2 (154 µL, 16.6 nmols) with stirring. The pH was adjusted to about 6.8 by the addition of 12.5 µL of sodium carbonate (1.0 M solution), the reaction was continued for 1 hr at room temperature and terminated with the addition of 100 µL of cysteamine (0.4 mM solution). The conjugation mixture was purified on a CM cellulose column with a sodium chloride gradient elution.

Preparation of IgG-Asymmetrical Randomly Branched Polymer Conjugates

The preparation of randomly branched mixed surface (OH/NH$_2$ mix) m-ran-AB-PEI-NH$_2$/OH-2-IgG conjugates is provided as a general procedure for the preparation of polymer-antibody and polymer-streptavidin conjugates. Other conjugates such as PEI-IgG, m-ran-AB-PEI-NH$_2$-1-IgG, m-ran-AB-PEI-NH$_2$-2-IgG, m-ran-AB-PEI-NH$_2$-3-IgG, m-ran-AB-PEI-NH$_2$-4-IgG, as well as m-ran-AB-PEI-NH$_2$/OH-1 (OH/NH$_2$ mix)-IgG, m-ran-AB-PEI-NH$_2$/OH-2 (OH/NH$_2$ mix)-IgG, m-ran-AB-PEI-NH$_2$/OH-3 (OH/NH$_2$ mix)-IgG, regular polylysine polymer, alkyl modified random branched poly(2-ethyloxazoline) with primary amine chain ends were all synthesized in a similar manner. The synthesis of various protein conjugates with asymmetrically random branched PEOX polymers also is conducted in a similar manner. The biotinylated-IgG conjugates were synthesized as provided in Bioconjugate Techniques (G. Hermanson, Academic Press, 1996).

LC-SPDP-Mixed Surface m-Ran-AB-PEI-NH$_2$/OH-2

To the mixed surface randomly branched m-ran-AB-PEI-NH$_2$/OH-2 (4×10$^{-7}$ mol) in 400 µl of phosphate buffer (20 mM phosphate and 0.1 M NaCl, pH 7.5) were added 4.0×10$^{-6}$ mol of sulfo-LC-SPDP (Pierce, IL) in 400 µl of water. That was vortexed and incubated at 30° C. for 30 minutes. The LC-SPDP-m-ran-AB-PEI-NH$_2$/OH-2 was purified by gel filtration chromatography and equilibrated with buffer A (0.1 M phosphate, 0.1 M NaCl and 5 mM EDTA, pH 6.8). The product was concentrated further to yield 465 µl of solution with a concentration of approximately 0.77 nmol/µmol.

Thiolated m-Ran-AB-PEI-NH$_2$/OH-2 from LC-SPDP m-Ran-AB-PEI-NH$_2$/OH-2

The LC-SPDP m-ran-AB-PEI-NH$_2$/OH-2 (50 nmol in 65 ml of buffer A) was mixed with 100 µL of dithiothreitol (DTT) (50 mM in buffer A) and was allowed to incubate at room temperature for 15 minutes. Excess DTT and byproducts were removed by gel filtration with buffer A. The product was concentrated in a 10 K Centricon Concentrator to yield 390 µL of the thiolated m-ran-AB-PEI-NH$_2$/OH-2 that was used for conjugation with activated antibody.

Maleimide-R-activated antibody made as described above was used for conjugation with the thiolated m-ran-AB-PEI-NH$_2$/OH-2.

m-Ran-AB-PEI-NH$_2$/OH-2-Antibody Conjugate

To the thiolated m-ran-AB-PEI-NH$_2$/OH-2 (310 µL or 35.7 nmol) was added the MAL-R-activated antibody (4.8 mL or 34 nmol). The reaction mixture was concentrated to approximately 800 µL and allowed to incubate overnight at 4° C. and/or at room temperature for about 1 hr. On completion, the reaction was quenched with 100 µL of ethyl maleimide (50 mmolar solution) and the conjugate then was fractionated on a carboxymethyl cellulose column (5 ml) with a sodium chloride step gradient in 20 mM phosphate buffer at pH 6. The conjugate was eluted with a sodium chloride gradient and characterized by cationic exchange chromatography, UV spectroscopy and polyacrylamide gel electrophoresis.

Paclitaxel Formulation and Nanoparticle Preparation

Paclitaxel was dissolved in ethanol to a concentration of up to 40 mg/mL.

A $C_{18}$ hydrocarbon modified randomly branched PEOX was prepared as taught herein.

The polymer was separately dissolved to a concentration of up to 100 mg/mL in saline. The two solutions were then mixed at various volumes to result in final polymer to paclitaxel molar ratios in the mixtures ranging from 3:1 to 10:1. The mixtures were subsequently frozen at −80° C. for 3 hours then lyophilized for 20 to 48 hours depending on volume.

The size of the aggregates as measured by light scattering ranged from about 120 nm to about 165 nm in diameter.

Alternatively, both paclitaxel and the PEOX polymer can be dissolved in a common solvent, such as, acetone and then dropwise added to water while being stirred or sonicated, followed by dialysis with a 1000 MW cutoff membrane. The final product then can be generated by lyophilization and the size of the aggregates was measured by light scattering.

Other PAA induced aggregates or nanoparticles using various hydrophobically surface modified branched polymers, such as, $C_4$, $C_6$, $C_{12}$ or $C_{22}$ hydrocarbon modified randomly branched PEOX, PEI and PPI polymers; $C_4$, $C_6$, $C_{12}$, $C_{18}$ and $C_{22}$ hydrocarbon modified PAMAM, PEI and PPI dendrimers and dendrigrafts; and $C_4$, $C_6$, $C_{12}$, $C_{18}$ and $C_{22}$ hydrocarbon modified branched PLL/polymers can be prepared in a similar manner.

Thus, $C_{18}$-PEOx-100-$NH_2$ (500 mg) is dissolved in 5 mL of ethanol to yield a 100 mg/mL solution. A 20 mg/mL solution of Paclitaxel is also prepared by dissolving 100 mg in 5 mL of ethanol. The two solutions are mixed for 20 minutes resulting in a solution containing 10 mg Paclitaxel and 50 mg polymer per mL, providing a solution with a 1:5 drug:polymer ratio. The mixture is placed on a rotary evaporator and the ethanol removed to dryness. The resultant solid is redissolved with stirring in 33 mL of saline solution to a final Paclitaxel concentration of 3 mg/mL. The solution preparation is passed through a 0.8 μm filter and then a 0.22 μm filter. The filtrate is frozen in a vial at −70° C. for at least 2 hours then lyophilized over a 72 hour period. The vial is stoppered and the ready-to-use white powder is stored at room temperature.

Nanoparticle Measurement

The size of various polymers, polymer only aggregates, as well as drug-induced polymer aggregates was measured by a dynamic light scattering method using a Malvern Zetasizer Nano-ZS Zen3600 particle size analyzer.

Activity Testing

Metabolism in viable cells produces "reducing equivalents," such as, NADH or NADPH. Such reducing compounds pass electrons to an intermediate electron transfer reagent that can reduce the tetrazolium product, MTS (Promega), into an aqueous, soluble formazan product, which is colored. At death, cells rapidly lose the ability to reduce tetrazolium products. The production of the colored formazan product, therefore, is proportional to the number of viable cells in culture.

The CellTiter 96® Aqueous products (Promega) are MTS assays for determining the number of viable cells in culture. The MTS tetrazolium is similar to MTT tetrazolium, with the advantage that the formazan product of MTS reduction is soluble in cell culture medium and does not require use of a solubilization solution. A single reagent added directly to the assay wells at a recommended ratio of 20 μl reagent to 100 μl of culture medium was used. Cells were incubated 1-4 hours at 37° C. and then absorbance was measured at 490 nm.

Thus, the cytotoxicity of various paclitaxel containing aggregates of interest, along with commercially available Taxol and Abraxane, a paclitaxel nanoparticle encapsulated with human serum albumin, were tested on different cancer cell lines (from ATCC) including, lung cancer A549, breast cancer MDA-MB-231 and OV 90 ovarian cancer cell lines, as well as on a normal human fibroblast cell line.

The drug-induced nanoparticles were at least the same or more potent at killing the cancer cells, particularly at low drug concentrations ranging from 0.5 μg/mL to 0.5 ng/mL. No toxicity to the normal human fibroblast cell line was observed.

The maximum tolerated dose (MTD) of the drug-induced nanoparticles was compared to that of Taxol. Over the course of seven weeks, various doses of Taxol and the paclitaxel-containing nanoparticles of interest were injected into the tail vein of CD-1 mice. The MTD of the paclitaxel nanoparticles was more than 7-fold higher than that of Taxol, with no major side effects to the surviving mice. Also, significant weight loss was observed in mice receiving Taxol as compared to no weight loss for the cohort that received the paclitaxel nanoparticles of interest.

A controlled study using lung cancer A548 cell line and breast cancer MDA-MB-231 cell line in a xenograft mouse model revealed that the paclitaxel nanoparticles inhibited tumor growth in vivo significantly better than did Taxol and Abraxane. A rapid reduction of tumors in mice receiving the paclitaxel nanoparticles of interest was observed, as compared to mice receiving Taxol or Abraxane.

Campothecin Formulation and Nanoparticle Preparation

Camptothecin (2.1 mg) and polymer (10.5 mg) are dissolved in a 4:1 v/v chloroform:ethanol mixture. Following thorough mixing, the solvent is removed to dryness on a rotary evaporator. The resultant solid mixture is redissolved in 2 mL of saline solution, mixed, then filtered through a 0.8 um syringe filter. The filtrate is frozen at −70° C. for at least 2 hours in a lyophilization vial, then lyophilized overnight (~16 hours). The vial is stoppered and the ready-to-use white powder is stored at −70° C. The material is reconstituted with 2 mL of water immediately prior to use.

Irinotecan, also known as CPT-11, is a synthetic analog of camptothecin. CPT-11 contains, for example, a bipiperdine carboxylate group and an ethyl group on the A and B rings, to yield a compound with greater cytotoxicity than the parent molecule.

Varying concentrations of CPT-11 and the camptothecin branched polymer aggregates described above were prepared.

Two cancer cell lines were maintained in suitable medium under recognized culture conditions. MCF-7 is a human breast cancer cell line and H460 is a human epithelial lung cancer cell line. Those cell lines were exposed to varying concentrations of CPT-11 and concentrations of the camptothecin aggregates based on the amount of drug. Cell survivability was assessed as described above.

Figure 17:
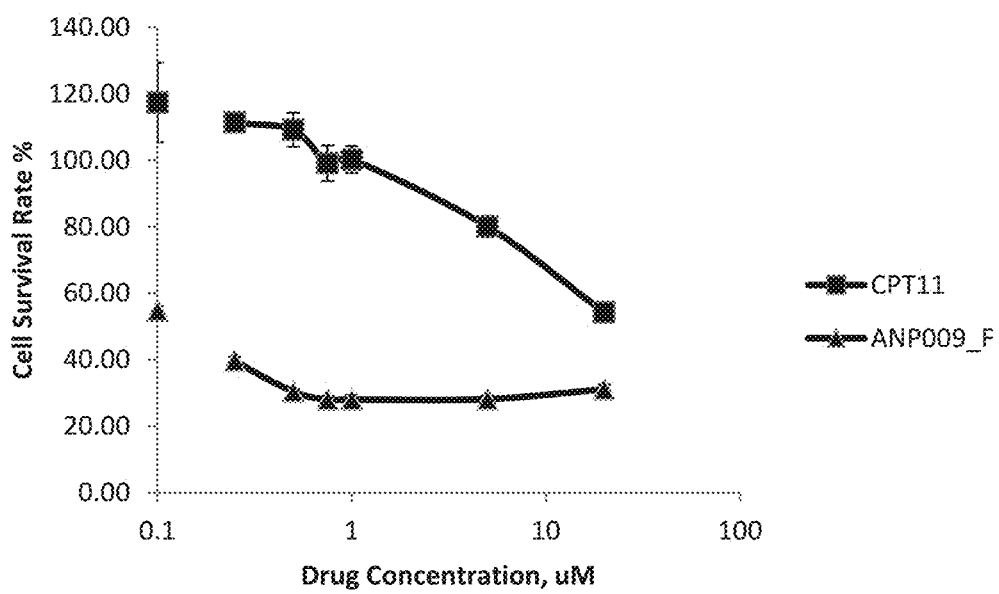
FIG. 17 summarizes data comparing cytotoxicity of a drug and a drug aggregate. MCF-7 human breast cancer cells were exposed to various concentrations of each and survivability was determined.

FIG. 17 summarizes results obtained with the MCF-7 breast cancer cell line. It can be seen that cytotoxicity of the cells to CPT-11 increased with increasing drug concentration. On the other hand, the camptothecin aggregate was more highly cytotoxic at all dosages tested. Polymer not associated with drug was not cytotoxic. Thus, although camptothecin per se does not have the same level of cytotoxicity as does CPT-11, when aggregated with a branched polymer, that aggregate was more cytotoxic than CPT-11.

Figure 18:
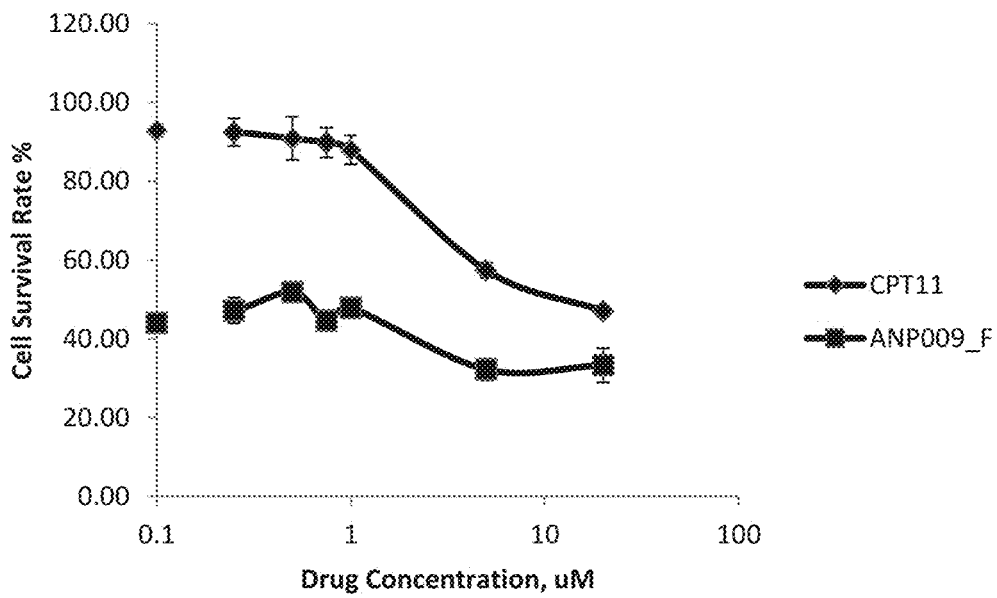
FIG. 18 summarizes data comparing cytotoxicity of a drug and a drug aggregate. H460 human epithelial lung cancer cells were exposed to various concentrations of each and survivability was determined.

A similar result was obtained with the H460 lung cancer cell line. As depicted in FIG. 18, a dose response curve of cytotoxicity to CPT-11 was observed. However, the camptothecin/branched polymer aggregates were more cytotoxic than CPT-11 at each concentration tested.

All references cited herein are herein incorporated by reference in entirety.

It will be appreciated that various changes and modifications can be made to the teachings herein without departing from the spirit and scope of the disclosure.

The invention claimed is:

1. A lyophilized aggregate comprising: a paclitaxel and a polymer comprising a random asymmetrically branched poly(2-substituted) oxazoline modified with a $C_{18}$ aliphatic chain surface group, wherein said lyophilized aggregate comprises a polymer to paclitaxel molar ratio of 5:1 and said paclitaxel is located at said surface group.

2. The lyophilized aggregate of claim 1, wherein said poly(2-substituted oxazoline) comprises poly(2-methyloxazoline), poly(2-ethyloxazoline), poly(2-propyloxazoline) or poly(2-butyloxazoline).

3. The lyophilized aggregate of claim 1, wherein said lyophilized aggregate is water soluble.

4. The lyophilized aggregate of clam 1, wherein said polymer comprises an amine group.

5. The lyophilized aggregate of claim 1, further comprising a targeting moiety.

6. A composition comprising the lyophilized aggregate of claim 1 and an aqueous solution.

7. A composition comprising the lyophilized aggregate of claim 1 and a pharmaceutically acceptable carrier, excipient or diluent.

8. The composition of claim 7, wherein said pharmaceutically acceptable carrier, excipient or diluent is selected from the group consisting of water, saline and phosphate-buffered saline (PBS).

* * * * *